United States Patent
Sigl et al.

(10) Patent No.: US 9,266,808 B2
(45) Date of Patent: Feb. 23, 2016

(54) METHOD FOR THE HYDROFORMYLATION OF OLEFINS

(75) Inventors: Marcus Sigl, Mannheim (DE); Frank Poplow, Ludwigshafen (DE); Rainer Papp, Speyer (DE); Thomas Mackewitz, Singapore (SG); Dag Wiebelhaus, Nuestadt (DE); Rocco Paciello, Bad Durkheim (DE); Thomas Heldemann, Viemheim (DE); Frank Heimann, Ludwigshafen (DE); Stefan Bitterlich, Dirmstein (DE); Martin Volland, Jersey City, NJ (US); Sven Crone, Limburgerhof (DE); Christoph Obler, Lautersheim (DE)

(73) Assignee: BASF SE (DE)

( * ) Notice: Subject to any disclaimer, the term of this patent is extended or adjusted under 35 U.S.C. 154(b) by 1029 days.

(21) Appl. No.: 12/516,855

(22) PCT Filed: Nov. 29, 2007

(86) PCT No.: PCT/EP2007/063010
§ 371 (c)(1),
(2), (4) Date: May 29, 2009

(87) PCT Pub. No.: WO2008/065171
PCT Pub. Date: Jun. 5, 2008

(65) Prior Publication Data
US 2010/0048959 A1   Feb. 25, 2010

(30) Foreign Application Priority Data
Nov. 30, 2006  (EP) ..................................... 06125151

(51) Int. Cl.
| C07C 29/141 | (2006.01) |
| C07C 45/50  | (2006.01) |
| C07C 5/25   | (2006.01) |
| C07C 45/74  | (2006.01) |

(52) U.S. Cl.
CPC ............... *C07C 45/50* (2013.01); *C07C 5/2506* (2013.01); *C07C 29/141* (2013.01); *C07C 45/74* (2013.01)

(58) Field of Classification Search
CPC .................................................. C07C 29/141
USPC ........................................ 568/450, 454, 909
See application file for complete search history.

(56) References Cited

U.S. PATENT DOCUMENTS

| | | |
|---|---|---|
| 3,193,596 A | 7/1965 | Bown et al. |
| 3,475,511 A | 10/1969 | Manning |
| 3,485,887 A | 12/1969 | Kronig et al. |
| 4,229,610 A | 10/1980 | Myers et al. |
| 4,289,919 A | 9/1981 | Myers |
| 4,409,418 A | 10/1983 | Johnson et al. |
| 4,426,542 A | 1/1984 | Barker et al. |
| 4,499,326 A | 2/1985 | Melquist |
| 4,517,395 A | 5/1985 | Obenaus et al. |
| 4,668,651 A | 5/1987 | Billig et al. |
| 4,748,261 A | 5/1988 | Billig et al. |
| 4,749,819 A | 6/1988 | Hamilton, Jr. |
| 4,769,498 A | 9/1988 | Billig et al. |
| 4,801,738 A | 1/1989 | Schneider et al. |
| 4,814,542 A | 3/1989 | Forlani et al. |
| 4,885,401 A | 12/1989 | Billig et al. |
| 4,992,613 A | 2/1991 | Brownscombe |
| 5,242,550 A | 9/1993 | Asselineau et al. |
| 5,268,514 A | 12/1993 | Bahrmann et al. |
| 5,288,370 A | 2/1994 | Asselineau et al. |
| 5,463,147 A | 10/1995 | Bahrmann et al. |
| 5,936,131 A | 8/1999 | Teissier et al. |
| 6,573,414 B2 | 6/2003 | McAtee et al. |
| 6,753,450 B2 | 6/2004 | Ahlers et al. |
| 6,835,855 B2 | 12/2004 | Ahlers |
| 6,852,661 B1 | 2/2005 | Ahlers et al. |
| 6,875,901 B2 * | 4/2005 | Gartside et al. ............... 585/670 |
| 6,881,867 B2 | 4/2005 | Ahlers et al. |
| 6,977,312 B2 | 12/2005 | Ahlers et al. |
| 7,173,138 B2 | 2/2007 | Ahlers et al. |
| 7,485,761 B2 | 2/2009 | Schindler |
| 7,615,645 B2 | 11/2009 | Volland et al. |
| 2004/0181111 A1 | 9/2004 | Sigl |
| 2006/0224000 A1 | 10/2006 | Papp et al. |

(Continued)

FOREIGN PATENT DOCUMENTS

| CA | 1222529 A | 6/1987 |
| CA | 2442039 A1 | 10/2002 |

(Continued)

OTHER PUBLICATIONS

Applied Catalysis A: General 212 (2001) 61-81 "Decomposition pathways of homogeneous catalysts", Piet W. N.M. Van Leeuwen.
Chem. Eur. J. 1999, 5, No. 4 "Dual Catalytic Systems for Consecutive Isomerization—Hydroformylation Reactions", Matthias Beller, et al.
DGMK, German Society for Petroleum and Coal Science and Technology, "Proceedings of the DGMK—Conference—Creating Value from Light Olefins—Production and Conversion" Oct. 10-12, 2001, Hamburg, Germany, edited by G. Emig, et al.
European office action mailed Aug. 20, 2015.

*Primary Examiner* — Sikarl Witherspoon
(74) *Attorney, Agent, or Firm* — Drinker Biddle & Reath LLP

(57) ABSTRACT

The present invention relates to a process for preparing hydroformylation products of olefins having at least four carbon atoms, in which a high proportion of both the linear $C_i$-olefins having a terminal double bond comprised in the olefin-comprising feed used and of the linear $C_i$-olefins having an internal double bond is converted into hydroformylation products. Furthermore, the invention relates to a process for preparing 2-propylheptanol which comprises such a hydroformylation process.

1 Claim, 2 Drawing Sheets

(56) References Cited

U.S. PATENT DOCUMENTS

2006/0293549 A1 12/2006 Sigl
2008/0033223 A1 2/2008 Sigl

FOREIGN PATENT DOCUMENTS

| | | | |
|---|---|---|---|
| CN | 1280976 | A | 1/2001 |
| DE | 1568542 | | 5/1970 |
| DE | 10035120 | A1 | 1/2001 |
| DE | 10035370 | A1 | 3/2001 |
| DE | 10023471 | A1 | 11/2001 |
| DE | 102 43 138.8 | | 3/2004 |
| DE | 103 42 760 | A1 | 3/2004 |
| EP | 0016286 | A2 | 10/1980 |
| EP | 0080449 | A1 | 6/1983 |
| EP | 0081041 | A1 | 6/1983 |
| EP | 0125567 | A1 | 11/1984 |
| EP | 0129899 | B1 | 8/1987 |
| EP | 0234498 | B1 | 8/1990 |
| EP | 0562451 | A2 | 9/1993 |
| EP | 0646563 | A1 | 4/1995 |
| EP | 0671419 | A1 | 9/1995 |
| EP | 0718036 | A1 | 6/1996 |
| EP | 0751106 | A1 | 1/1997 |
| EP | 0792862 | B1 | 3/2001 |
| EP | A 1466881 | | 10/2004 |
| JP | 51108691 | | 9/1976 |
| WO | WO-84/03697 | A1 | 9/1984 |
| WO | WO-00/56451 | A1 | 9/2000 |
| WO | WO-01/55065 | A1 | 8/2001 |
| WO | WO-01/58589 | A1 | 8/2001 |
| WO | WO-01/85661 | A1 | 11/2001 |
| WO | WO-01/85662 | A2 | 11/2001 |
| WO | WO-02/22261 | A2 | 3/2002 |
| WO | WO-02/083695 | A1 | 10/2002 |
| WO | WO-02/096843 | A1 | 12/2002 |
| WO | WO-03/018192 | A2 | 3/2003 |
| WO | WO 2004/102488 | | 5/2004 |
| WO | WO-2005/039762 | A1 | 5/2005 |
| WO | WO-2005/042458 | A2 | 5/2005 |
| WO | WO 2006/024366 | | 2/2008 |
| WO | WO 2005/042449 | | 2/2009 |

\* cited by examiner

METHOD FOR THE HYDROFORMYLATION OF OLEFINS

RELATED APPLICATIONS

This application is a national stage application (under 35 U.S.C. §371) of PCT/EP2007/063010, filed Nov. 29, 2007, which claims benefit of European application 06125151.8, filed Nov. 30, 2006.

BACKGROUND OF THE INVENTION

The present invention relates to a process for preparing hydroformylation products of olefins having at least four carbon atoms, in which a high proportion of both the linear $C_i$-olefins having a terminal double bond comprised in the olefin-comprising feed used and of the linear $C_i$-olefins having an internal double bond is converted into hydroformylation products. Furthermore, the invention relates to a process for preparing 2-propylheptanol which comprises such a hydroformylation process.

Hydroformylation or the oxo process is an important industrial process and is employed for preparing aldehydes from olefins, carbon monoxide and hydrogen. These aldehydes can, if appropriate, be hydrogenated by means of hydrogen to give the corresponding oxo alcohols in the same process. The reaction itself is strongly exothermic and generally proceeds under superatmospheric pressure and at elevated temperatures in the presence of catalysts. Catalysts used are Co, Rh, Ir, Ru, Pd or Pt compounds or complexes which can be modified with N- or P-comprising ligands to influence the activity and/or selectivity. In the case of the hydroformylation reaction of olefins having more than two carbon atoms, mixtures of isomeric aldehydes can be formed as a result of the possible addition of Co to each of the two carbon atoms of a double bond. In addition, when olefins having at least four carbon atoms are used, double bond isomerization, i.e. shifting of internal double bonds to a terminal position and vice versa, can also occur.

Owing to the significantly greater industrial importance of the α-aldehydes, optimization of the hydroformylation process so as to achieve very high conversions combined with a very low tendency to form olefins having double bonds which are not in the α position is sought. In addition, there is a need for hydroformylation processes which, even starting out from internal or linear olefins, lead to α- and in particular n-aldehydes in good yields. Here, the catalyst used has to make both the establishment of an equilibrium between internal and terminal double bond isomers and the very selective hydroformylation of the terminal olefins possible.

Thus, for example, there is a need for plasticizer alcohols having from about 6 to 12 carbon atoms and a low degree of branching (known as semilinear alcohols) and corresponding mixtures thereof for the production of ester plasticizers having good use properties. These include, in particular, 2-propylheptanol and alcohol mixtures comprising this. They can be prepared, for example, by subjecting $C_4$-hydrocarbon mixtures comprising butenes or butenes and butanes to hydroformylation and subsequent aldol condensation. When hydroformylation catalysts having an insufficient n selectivity are used, the hydroformylation can easily result in formation of not only n-valeraldehyde but also undesirable product aldehydes, which adversely affects the economics of the entire process.

The use of phosphorus-comprising ligands for stabilizing and/or activating the catalyst metal in rhodium-catalyzed low-pressure hydroformylation is known. Suitable phosphorus-comprising ligands are, for example, phosphines, phosphinites, phosphonites, phosphites, phosphoramidites, phospholes and phosphobenzenes. The most widespread ligands at present are triarylphosphines such as triphenylphosphine and sulfonated triphenylphosphine since these have a satisfactory activity and stability under the reaction conditions. However, these ligands have the disadvantage that they generally give satisfactory yields, in particular of linear aldehydes, only in the presence of very large excesses of ligand and internal olefins are not reacted to any appreciable extent.

On the other hand, it has been reported that particular catalysts make hydroformylation of linear olefins with increased selectivity to unbranched reaction products possible. Thus, U.S. Pat. Nos. 4,668,651, 4,748,261, 4,769,498 and 4,885,401 disclose particular rhodium/bisphosphite catalysts which allow hydroformylation of various linear olefins, e.g. propylene, butenes and hexenes, with sometimes good selectivity to unbranched reaction products. The conversion of olefins having an internal double bond into linear hydroformylation products can sometimes also be successfully carried out using the rhodium/bisphosphite catalysts described there.

J. Kolena, P. Morávek, J. Lederer, DGMK Tagungsbericht (2001), 2001-4 (Proceedings of the DGMK Conference "Creating Value from Light Olefins—Production and Conversion", 2001), 119-126, it is mentioned on page 121 that rhodium/bisphosphite catalysts as are described in the abovementioned US patent texts have been used in Union Carbide's UNOXOL 10 process for preparing 2-propylheptanol from raffinate II.

A similar process for preparing 2-propylheptanol using 2-butene is described in the patent application WO 03/018192, where chelating phosphordiamidites are used as cocatalysts.

The abovementioned processes using specific rhodium/bisphosphite catalysts have the advantage of partial utilization of olefins having an internal double bond, but the phosphite ligands used or their derivatives have the disadvantage that they undergo various degradation reactions under customary hydroformylation and/or distillation conditions. These include, for example, hydrolysis, alcoholysis, transesterification, Arbusov rearrangement and reaction with cleavage of O—C and P—O bonds, as are described in P. W. N. M. van Leeuwen, Appl. Cat. A: General 2001, 212, 61.

In the process described in U.S. Pat. No. 4,426,542, the hydroformylation is carried out using cobalt catalyst under high-pressure conditions, as a result of which utilization of olefins having an internal double bond is likewise made possible. However, the proportion of n compounds in the hydroformylation products obtained is comparatively low. In addition, the process comprises a step which is carried out under high pressure. The capital costs for high-pressure processes are significantly higher than for low-pressure processes, so that the process is economically disadvantaged.

To achieve virtually complete utilization of olefins in olefin mixtures such as raffinate II using stable rhodium/phosphane catalysts, the process variant described in WO 01/55065 A1 has been developed. This describes a process for the integrated preparation of $C_9$-alcohols and $C_{10}$-alcohols from raffinate II, in which the butenes comprised in the raffinate II are largely utilized in the hydroformylation step, However, only the α-olefin 1-butene in the raffinate II is utilized for producing the $C_{10}$-alcohol by means of aldol condensation and hydrogenation. Utilization of the 2-butene is achieved only by means of unavoidable coproduction of $C_9$-alcohols.

If the hydroformylation is carried out as a single-stage process, complete or virtually complete conversions of the olefins used into preferably linear hydroformylation products can therefore frequently not be realized for technical reasons or reasons of process economics. This applies particularly to the use of olefin mixtures which comprise olefins of differing reactivity, for example olefins having internal double bonds and olefins having terminal double bonds. Processes in which the hydroformylation is carried out in two or more reaction stages have therefore been developed. Here, the reactors are, for example, in the form of a cascade in which the individual reactors are operated under different reaction conditions. In this way, it is possible, at a given reaction volume, to achieve a higher conversion than in an individual reactor of the same volume. Thus, for example, DE-A-100 35 120 and DE-A-100 35 370 describe processes for the hydroformylation of olefins in a two-stage reaction system.

EP-A-0 562 451 and EP-A-0 646 563 describe processes for preparing mixtures of isomeric decyl alcohols by two-stage hydroformylation of an olefin mixture comprising 1-butene and 2-butene, aldol condensation of the resulting aldehyde mixture and subsequent hydrogenation. In the process described in EP-A-0 562 451, the first stage predominantly converts 1-butene into valeraldehyde with an n selectivity of greater than 90%, while the unreacted olefins, predominantly 2-butene, are converted into n- and i-valeraldehyde in the second reaction stage. The second stage gives a valeraldehyde having a comparatively low proportion of the n compound. The total proportion of n compounds is thus significantly less than 90%. In addition, the process comprises a step which is carried out at high pressure. The capital costs for high-pressure processes are significantly higher than for low-pressure processes, so that the process is economically disadvantaged.

It is generally known that the isomerization of 2-butenes to 1-butene is an equilibrium reaction. Cis-2-butene, trans-2-butene and 1-butene are present in equilibrium with one another. The thermodynamic data are presented in D. Stull, "The Chemical Thermodynamics of Organic Compounds", J. Wiley, New York 1969. An appropriate combination of isomerization and hydroformylation enabled the utilization possibilities for olefins having an internal double bond and for olefin mixtures comprising such olefins to be considerably improved.

Thus, Beller et al. in Chem. Eur. J. 5 (1999), 1301-1305, describe a process in which an isomerization step and a hydroformylation step are carried out in parallel. Here, two different homogeneous catalyst systems are used in one reactor. One of these catalyzes the isomerization and the other catalyzes the hydroformylation. A disadvantage of this process is that the two catalysts have to be matched to one another in a complicated fashion.

A process sequence in which the isomerization step and the hydroformylation step are carried out separately therefore comes into consideration. Although the double bond isomerization of olefins is known per se, specific requirements have to be taken into account in an industrial reaction which requires efficient coupling with a hydroformylation stage.

For example, U.S. Pat. No. 4,409,418 teaches that internal olefins can be isomerized to terminal olefins over Zr phosphates which are doped with Cr and/or Th.

It is known from EP-A-751 106 that 1-butene can be obtained from a $C_4$-hydrocarbon stream by subjecting the $C_4$-hydrocarbon stream to a selective hydrogenation and a fractional distillation, separating off a pure 1-butene fraction and then separating off the paraffins from the remaining 2-butene-comprising fraction by means of a molecular sieve and subjecting the resulting olefin-comprising stream to a double bond isomerization and recirculating it to the selective hydrogenation. A disadvantage of this process is that the fraction which has been subjected to the isomerization is recirculated to the hydrogenation step instead of directly to the distillation step. As a result, the volume of the circulating stream is inflated and the reactor in which the hydrogenation is carried out is burdened to a high degree with compounds which are inert toward the hydrogenation and are removed only in the subsequent distillation.

WO 02/096843 describes a process for obtaining 1-butene from 2-butenes. Here, a hydrocarbon stream comprising mainly 2-butenes is subjected to an isomerization and the reaction mixture formed is subjected to a distillation. In the distillation, a 1-butene-rich stream is separated off from a 2-butene-rich stream and the latter is recirculated to the isomerization step. However, this process is uneconomical for a hydrocarbon stream which comprises significant amounts of 1-butene. As a result of the distillation being carried out after the isomerization step, interfering volatile constituents of the feed (e.g. alkynes) can get into the isomerization reactor and there damage the catalyst or lead to formation of undesirable by-products.

BRIEF SUMMARY OF THE INVENTION

The invention accordingly provides a process for the hydroformylation of olefins having at least four carbon atoms, in which an olefin-comprising feed comprising a linear $C_i$-olefin having a terminal double bond and at least one linear $C_i$-olefin having an internal double bond, where i is an integer of at least 4, is used and subjecting the olefin-comprising feed to a hydroformylation, wherein the content of linear $C_i$-olefin having a terminal double bond in the stream fed to the hydroformylation stage is increased by means of a double bond isomerization by subjecting (I) firstly a part of the olefin-comprising feed to the double bond isomerization before the hydroformylation, with a stream enriched in linear $C_i$-olefin having an internal double bond being fed to the double bond isomerization stage; or (II) the olefin-comprising feed firstly to the hydroformylation, separating off a stream comprising unreacted linear $C_i$-olefin having an internal double bond from the output from the hydroformylation stage and subjecting at least part of the stream which has been separated off to the double bond isomerization;

and the output or part of the output from the double bond isomerization is used for providing the stream fed to the hydroformylation stage.

It was therefore an object of the present invention to provide an efficient process for the hydroformylation of olefins having at least four carbon atoms which starts out from mixtures of olefins having terminal and internal double bonds, in particular raffinate II, and comprises a double bond isomerization. The process of the invention should allow very substantial utilization both of the olefins having a terminal double bond and those having an internal double bond. In addition, it should lead to a very high proportion of unbranched hydroformylation products, i.e. have a high n selectivity. Furthermore, the process of the invention should allow the processing of the hydroformylation products by means of aldol condensation and hydrogenation to give mixtures of alcohols having 10 or more carbon atoms.

It has surprisingly been found that such a process can be carried out efficiently when the content of linear olefins having a terminal double bond in the stream fed to the hydroformylation stage is increased by means of a double bond isomerization, with the double bond isomerization stage being carried out either before or after the hydroformylation stage.

DETAILED DESCRIPTION OF THE INVENTION

The present invention accordingly provides a process for the hydroformylation of olefins having at least four carbon atoms, in which an olefin-comprising feed comprising a linear $C_i$-olefin having a terminal double bond and at least one linear $C_i$-olefin having an internal double bond, where i is an integer of at least 4, is used and the olefin-comprising feed is subjected to a hydroformylation, wherein the content of linear $C_i$-olefin having a terminal double bond in the stream fed to the hydroformylation stage is increased by means of a double bond isomerization by subjecting (I) firstly a part of the olefin-comprising feed to the double bond isomerization before the hydroformylation, with a stream enriched in linear $C_i$-olefin having an internal double bond being fed to the double bond isomerization stage; or (II) the olefin-comprising feed firstly to the hydroformylation, separating off a stream comprising unreacted linear $C_i$-olefin having an internal double bond from the output from the hydroformylation stage and subjecting at least part of the stream which has been separated off to the double bond isomerization;

and the output or part of the output from the double bond isomerization is used for providing the stream fed to the hydroformylation stage.

A first embodiment relates to a process for hydroformylation of olefins having at least 4 carbon atoms, in which an olefin-comprising feed comprising a linear $C_i$-olefin having a terminal double bond and at least one linear $C_i$-olefin having an internal double bond, where i is an integer of at least 4 is provided;

the olefin-comprising feed is subjected to a separation to give a stream enriched in linear $C_i$-olefin having a terminal double bond and a stream enriched in linear $C_i$-olefin having an internal double bond;

at least part of the stream enriched in linear $C_i$-olefin having an internal double bond is subjected to a double bond isomerization to increase the content of linear $C_i$-olefin having a terminal double bond;

at least part of the output from the double bond isomerisztion is used to provide a stream fed into the hydroformylation.

According to this embodiment at least part of the output from the double bond isomerization is preferably combined with the stream enriched in linear $C_i$-olefin having a terminal double bond obtained in the separation of the olefin-comprising feed and the combined streams are fed into the hydroformylation.

In order to achieve said combination, the separate streams can be mixed before introduction into the hydroformylation stage. In this specific embodiment the separation of the olefin-comprising feed is effected by means of distillation and the output from the double bond isomerization having an increased proportion of linear $C_i$-olefins having a terminal double bond is recirculated to the distillation apparatus. This recirculation is preferably carried out at a region of the distillation apparatus which has an increased content of linear $C_i$-olefin having a terminal double bond compared to the starting olefin-comprising feed fed in.

A second embodiment relates to a process for hydroformylation of olefins having at least 4 carbon atoms, in which an olefin-comprising feed comprising a linear $C_i$-olefin having a terminal double bond and at least one linear $C_i$-olefin having an internal double bond, where i is an integer of at least 4 is provided;

the olefin-comprising feed is subjected to a hydroformylation, wherein the output from the hydroformylation stage comprises unreacted linear $C_i$-olefins having an internal double bond;

a stream enriched in unreacted linear $C_i$-olefin having an internal double bond is separated off from the output from the hydroformylation stage;

at least part of the stream separated off is subjected to a double bond isomerization to increase the content of linear $C_i$-olefin having a terminal double bond;

at least part of the output from the double bond isomerization is introduced into the hydroformylation stage.

The process of the invention allows substantial utilization of the linear $C_i$-olefins, in particular those having an internal double bond, comprised in the olefin-comprising feed. The linear $C_i$-olefins comprised in the olefin-comprising feed are converted with high selectivity into linear hydroformylation products by means of the process of the invention. To achieve these advantages, it is an important aspect of the process of the invention according to the first embodiment that the linear $C_i$-olefins having an internal double bond comprised in the olefin-comprising feed are very largely firstly converted into linear $C_i$-olefins having a terminal double bond in the separate double bond isomerization stage before reaction in the hydroformylation stage. To achieve these advantages, it is an important aspect of the process of the invention according to the second embodiment that a stream enriched in unreacted linear $C_i$-olefin having an internal double bond is separated off from the output from the hydroformylation stage. At least a part of the stream enriched in unreacted linear $C_i$-olefin having an internal double bond which is separated off is subjected to a double bond isomerization to increase the content of linear $C_i$-olefin having a terminal double bond. Since in process step (II) the olefin-comprising feed is firstly fed to the hydroformylation, the conditions in the hydroformylation step when carrying out process step (II) will generally be set so that the $C_i$-olefins having an internal double bond which are present are not significantly reacted in this hydroformylation stage.

Suitable $C_i$-olefin starting materials for the olefin-comprising feed are in principle all linear (straight-chain) compounds which comprise at least 4, e.g. from 4 to 12 (i=4, 5, 6, 7, 8, 9, 10, 11 or 12), carbon atoms and at least one ethylenically unsaturated double bond. Here and in the following, the expression $C_i$-olefin refers to olefin compounds having i carbon atoms. Preference is given to $C_i$-olefin starting materials which comprise linear olefins having from 4 to 12 (i=4-12), particularly preferably from 4 to 8 (i=4-8) and very particularly preferably from 4 to 6 (i=4-6), carbon atoms.

According to the invention, the olefin-comprising feed comprises a linear $C_i$-olefin having a terminal double bond (here also referred to as α-olefins) and at least one corresponding linear $C_i$-olefin having an internal double bond, in particular a linear β-$C_i$-olefin. Thus, the olefin-comprising feed can, for a particular value of i, comprise, for example, two or three different linear $C_i$-olefins having an internal double bond; in the case of i=4, for example cis-2-butene and trans-2-butene. Examples of linear $C_i$-olefins having a terminal double bond are 1-butene, 1-pentene, 1-hexene, 1-heptene, 1-octene, 1-nonene, 1-decene, 1-undecene and 1-dodecene, with 1-butene, 1-pentene and 1-hexene being preferred among these. The feed particularly preferably comprises 1-butene. Examples of linear $C_i$-olefins having an internal double bond are 2-butenes, 2-pentenes, 2-hexenes, 3-hexenes, 2-heptenes, 3-heptenes, 4-heptenes, 2-octenes, 2-nonenes, 2-decenes, 2-undecenes, 2-dodecenes and mixtures thereof, with 2-butenes, 2-pentenes, 2-hexenes, 3-hexenes and mixtures thereof being preferred among these. The feed particularly preferably comprises 2-butenes. Very particular preference is given to using olefin mixtures which comprise at least one linear α-olefin having from 4 to 6 carbon atoms, in particular 1-butene, and also 2-butenes, 2-pentenes, 2-hexenes and/or mixtures thereof, in particular 2-butenes, and hydrocarbon mixtures which comprise such olefins. In addition, very particular preference is given to olefin mixtures which comprise essentially linear $C_i$-olefins which have the same value of it i.e. the same number of carbon atoms, e.g. 4, 5, 6, 7, 8, 9, 10, 11 or 12. The proportion of linear $C_i$-olefins having the same value of i is, in particular, in the range from 50 to 100% by weight and especially in the range from 55 to 99.9% by weight, in each case based on the total weight of the ethylenically monounsaturated or polyunsaturated hydrocarbons comprised in the hydrocarbon mixture or the olefin-comprising feed. The process of the invention is particularly advantageously carried out using olefin-comprising feeds in which the total proportion of saturated and ethylenically unsaturated hydrocarbons having precisely i carbon atoms is at least 90% by weight, e.g. in the range from 90 to 99.99% by weight, and especially at least 95% by weight, e.g. in the range from 95 to 99.9% by weight, in each case based on the total weight of the olefin-comprising feed.

The olefin-comprising feed used in the process of the invention is preferably an industrially available olefin-comprising hydrocarbon mixture.

Preferred industrially available olefin mixtures result from hydrocarbon cracking in petroleum processing, for example by catalytic cracking such as fluid catalytic cracking (FCC), thermal cracking or hydrocracking, with subsequent dehydrogenation. A suitable industrial olefin mixture is the $C_4$ fraction. $C_4$ fractions can be obtained, for example, by fluid catalytic cracking or steam cracking of gas oil or by steam cracking of naphtha. Depending on the composition of the $C_4$ fraction, a distinction is made between the total $C_4$ fraction (crude $C_4$ fraction), the raffinate I obtained after 1,3-butadiene has been separated off and the raffinate II obtained after isobutene has been separated off. A further suitable industrial olefin mixture is the $C_5$ fraction which can be obtained in naphtha cracking. Olefin-comprising mixtures of hydrocarbons having at least 4 carbon atoms which are suitable for use as olefin-comprising feed can also be obtained by catalytic dehydrogenation of suitable industrially available paraffin mixtures. $C_4$-Olefin mixtures can be prepared in this way from, for example, liquefied petroleum gas (LPG) and liquefied natural gas (LNG). The latter comprises not only the LPG fraction but also relatively large amounts of higher molecular weight hydrocarbons (light naphtha) and are thus also suitable for prepaing $C_5$- and $C_6$-olefin mixtures. Olefin-comprising hydrocarbon mixtures comprising monoolefins having at least 4 carbon atoms can be prepared from LPG or LNG streams by customary methods known to those skilled in the art, which generally comprise one or more work-up steps in addition to the dehydrogenation. These include, for example, the removal of at least part of the saturated hydrocarbons comprised in the abovementioned olefin feed mixtures. These can, for example, be reused for the preparation of olefin starting materials by cracking and/or dehydrogenation. However, the olefins used in the process of the invention can also comprise a proportion of saturated hydrocarbons which are inert under the hydroformylation conditions employed according to the invention. The proportion of these saturated components is generally not more than 60% by weight, preferably not more than 40% by weight, particularly preferably not more than 20% by weight, based on the total amount of olefins and saturated hydrocarbons comprised in the hydrocarbon feed material. Typical compositions of the abovementioned $C_4$ raffinates may be found in the literature, e.g. in EP-A-0 671 419 and in Schulz, Homann, "$C_4$-Hydrocarbons and Derivatives, Resources, Production, Marketing", Springer Verlag 1989.

A raffinate II suitable for use in the process of the invention has, for example, the following composition:
from 0.5 to 5% by weight of isobutane,
from 5 to 20% by weight of n-butane,
from 20 to 40% by weight of trans-2-butene,
from 10 to 20% by weight of cis-2-butene,
from 25 to 55% by weight of 1-butene,
from 0.5 to 5% by weight of isobutene
and also trace gases such as 1,3-butadiene, propene, propane, cyclopropane, propadiene, methylcyclopropane, vinylacetylene, pentenes, pentanes, etc., in the range of in each case a maximum of 1% by weight, e.g. in the range from 0.001 to 1% by weight, in each case based on the total weight of the raffinate II used. The proportion of the abovementioned trace gases in the raffinate II is generally in the range from 0.001 to 5% by weight, based on the total weight. If reference is made to butenes either here or in the following, the term always comprises, unless indicated otherwise, all butene isomers apart from isobutene.

In addition, oxygen-comprising compounds such as alcohols, aldehydes, ketones or ethers are advantageously largely removed from the olefin-comprising hydrocarbon mixture to be used. For this purpose, the olefin-comprising hydrocarbon mixture can advantageously be passed over an adsorbent, e.g. a molecular sieve, in particular one having a pore diameter of from >4 Å to 5 Å. The concentration of oxygen-comprising, sulfur-comprising, nitrogen-comprising and halogen-comprising compounds in the olefin-comprising hydrocarbon mixture is preferably not more than 1 ppm by weight and particularly preferably not more than 0.5 ppm by weight, in each case based on the total weight.

If multiply unsaturated hydrocarbon compounds such as diolefins or alkynes are present in the olefin-comprising hydrocarbon mixture to be used, these can be removed from the mixture down to an amount of preferably less than 10 ppm by weight, based on the total weight, before use as olefin-comprising feed. They are preferably removed by selective hydrogenation, e.g. as described in EP-81 041 and DE-15 68 542, particularly preferably by selective hydrogenation down to a residual content of not more than 5 ppm by weight and very particularly preferably not more than 1 ppm by weight, based on the total weight. Such a preceding hydrogenation can be particularly advantageous in the case of process step (II). When carrying out process step (I), on the other hand, it is advantageous to provide such a hydrogenation after the double bond isomerization step and before the hydroformylation step. The relevant details are discussed in more detail in the comprehensive discussion of the individual process steps and variants below.

According to the invention, the content of linear $C_i$-olefin having a terminal double bond in the stream fed to the hydroformylation stage is increased over its content in the olefin-comprising feed used by means of a double bond isomerization. In the isomerization stage, essentially linear $C_i$-olefins having an internal double bond are converted into olefins having a terminal double bond. Suitable substrates for such double bond isomerizations are, in particular, β-olefins, i.e. olefins which have a double bond between the 2 position and the 3 position of the linear chain composed of i carbon atoms. However, it has to be taken into account that such double bond isomerization reactions are limited by the thermodynamic equilibrium between the individual isomers. This determines the proportion of the respective linear isomer having a terminal double bond which can be achieved at a given temperature.

Thus, the achievable conversion in, for example, the isomerization of 2-butenes to 1-butene is limited by the proportion of the 1-butene isomer (or generally by the proportion of the n-isomers) in the thermodynamic equilibrium. The conversion of the 2-butenes into 1-butene by double bond isomerization is favored by higher temperatures. The maximum yields of 1-butene (2-butene conversion×selectivity) which can be achieved in a single pass through the reactor are limited by the position of the thermodynamic equilibrium at a temperature of 250° C. to about 16%, at a temperature of 400° C. to about 23% and at a temperature of 500° C. to about 30%. The yields indicated are based on the thermodynamic data published in D. Stull "The Chemical Thermodynamics of Organic Compounds", J. Wiley, New York, 1969. The process of the invention when $C_4$-olefin-comprising feeds are used therefore operates economically when the content of 1-butene in the stream fed to the isomerization stage is lower than the equilibrium concentration of 1-butene at the temperatures of the isomerization reaction, which are generally in the range from 100 to 700° C. To achieve this, a $C_4$-olefin-comprising feed which has a ratio of 2-butenes to 1-butene in the range from 6.1 to 0.1:1, preferably in the range from 3:1 to 0.2:1, is generally used for carrying out process step (I).

When carrying out the process of the invention with inclusion of process step (I), the stream fed to the hydroformylation stage is, according to the invention, provided by subjecting part of the olefin-comprising feed to the double bond isomerization and then feeding part or all of this to the hydroformylation, while the other part of the olefin-comprising feed is partly or completely fed directly to the hydroformylation stage. When carrying out the process of the invention with inclusion of the process step (II), the stream fed to the hydroformylation stage is, according to the invention, provided by feeding the olefin-comprising feed directly to the hydroformylation stage and additionally recirculating part of the output from the hydroformylation stage, after it has been subjected to the double bond isomerization, to the hydroformylation stage.

The way in which the invention is performed with inclusion of the process step (I) will be described in more detail below.

To carry out the process according to the variant with the process step (I), a part of the olefin-comprising feed is subjected to the double bond isomerization before the hydroformylation. For this purpose, e.g. a proportion in the range from 25 to 99% by weight, in particular in the range from 35 to 98% by weight and especially in the range from 50 to 95% by weight, in each case based on the total weight of the olefin-comprising feed, is used in the double bond isomerization stage. According to the invention, it is important in process step (I) that a stream which is enriched in the linear $C_i$-olefin having an internal double bond is fed to the isomerization stage. This makes it possible for the isomerization stage to be carried out efficiently, since the volume of the stream fed to the isomerization stage can be kept low and this fed stream comprises an increased proportion of those compounds which are actually to be reacted in the double bond isomerization stage. Other compounds comprised in the olefin-comprising feed, e.g. saturated hydrocarbons and linear $C_i$-olefins having a terminal double bond, should preferably not be fed to the isomerization stage. These compounds are therefore separated off, e.g. by means of distillation, from the olefin-comprising feed to the desired extent before the olefin-comprising feed is fed to the double bond isomerization stage. Part or all, preferably all, of the output from the double bond isomerization stage is fed to the hydroformylation stage. The part of the olefin-comprising feed which has not been fed to the double bond isomerization stage is fed, partly or completely, preferably essentially completely, e.g. a proportion in the range from 50 to 99.9% by weight, preferably in the range from 70 to 99% by weight, in each case based on the total weight of the part which has not been fed to the double bond isomerization stage, to the hydroformylation stage.

The linear $C_i$-olefins having a terminal double bond which are comprised in the olefin-comprising feed are suitable for direct introduction into the hydroformylation stage. It is therefore advantageous to separate these at least partly and preferably very substantially from the olefin-comprising feed, e.g. a proportion in the range from 10 to 99.9% by weight, preferably in the range from 25 to 99% by weight, in each case based on the total weight of the linear $C_i$-olefins having a terminal double bond in the olefin-comprising feed, before the isomerization stage. In this way, a very large proportion of the linear $C_i$-olefins having an internal double bond can be fed in an easily controllable manner to the double bond isomerization stage, e.g. a proportion of more than 50% by weight, preferably at least 75% by weight and particularly preferably at least 90% by weight, of the linear $C_i$-olefins having an internal double bond comprised in the olefin-comprising feed. This proportion of the olefin-comprising feed which is fed to the isomerization determines the achievable conversion of linear $C_i$-olefins having an internal double bond into olefins having a terminal double bond. This total conversion is generally in the range from 50 to 99.9% by weight, in particular in the range from 60 to 99.5% by weight and especially in the range from 70 to 99% by weight, in each case based on the total weight of linear $C_i$-olefins having an internal double bond in the olefin-comprising feed.

Furthermore, the abovementioned total conversion can also be increased by, in the isomerization reaction, firstly feeding unreacted linear $C_i$-olefins having an internal double bond again and if appropriate repeatedly, e.g. 3, 4, 5 times or more, to the isomerization stage. This can, for example, be effected by separating off linear $C_i$-olefins having a terminal double bond from the output from the isomerization stage, e.g. by distillation, and feeding these to the hydroformylation. The unreacted linear $C_i$-olefins having an internal double bond comprised in the output from the isomerization stage, which remain in this separation, are fed back into the isomerization stage.

A process variant in which a distillation stage and the isomerization stage are operated in parallel has been found to be particularly advantageous. In a preferred embodiment of the process of the invention, the olefin-comprising feed is therefore subjected to the process step (I), wherein Ia) the olefin-comprising feed is fed to a distillation column;
Ib) the stream enriched in linear $C_i$-olefin having an internal double bond is taken off in the lower part of the distillation column, at least part of the stream taken off is fed to a first reaction zone and reacted in the presence of a double bond isomerization catalyst;
Ic) the output from the first reaction zone is recirculated to the distillation column at a point above that at which the stream taken off in step Ib) is taken off; and
Id) a stream enriched in linear $C_i$-olefin having a terminal double bond is taken off in the upper part of the distillation column, the stream taken off is fed together with carbon monoxide and hydrogen to a second reaction zone and reacted in the presence of a hydroformylation catalyst.

The olefin-comprising feed is usually fed as a liquid or gaseous, preferably liquid, stream to the distillation column. If appropriate, the olefin-comprising feed can be heated before being fed into the distillation column, e.g. to a temperature in the range from >20 to 100° C. The olefin-comprising feed is preferably fed into the distillation column at room temperature or slightly above, e.g. in the range from 21 to 40° C. It is advantageously fed into the distillation column at a point within the upper two-thirds of the distillation column. The olefin-containing feed is advantageously fed in above the point at which the stream enriched in linear $C_i$-olefin having an internal double bond is taken off from the distillation column in step Ib).

As distillation column, it is possible to use any distillation column known to those skilled in the art which can be provided with inlets or outlets not only at the top and at the bottom of the column but also in the region of the remaining column body. Suitable columns are, for example, bubblecap tray columns, columns with random packing, columns with ordered packing or dividing wall columns. The distillation column preferably has a number of theoretical plates in the range from 30 to 80, particularly preferably in the range from 40 to 75. The reflux ratio is generally set to a value in the range from 5 to 75 and in particular in the range from 10 to 50. The distillation column is generally operated at a pressure in the range from 1 to 50 bar, in particular in the range from 2 to 40 bar and especially in the range from 5 to 20 bar. A temperature in the range from 40 to 180° C., in particular in the range from 50 to 150° C. and especially in the range from 60 to 120° C., is advantageously set in the bottom of the distillation column.

Owing to the generally lower boiling point of linear olefins having a terminal double bond (α-olefins), e.g. 1-butene, compared to the corresponding linear olefins having an internal double bond, in particular β-olefins such as 2-butenes, the α-olefins accumulate in the upper part of the column during the course of the distillation, while the β-olefins accumulate in the lower part of the column (together with any $C_i$-olefin isomers whose single double bond is located neither between the 1 and 2 position nor between the 2 and 3 position of the hydrocarbon chain of the respective $C_i$-olefin). The stream enriched in linear olefins having an internal double bond, in particular β-olefins, which is taken off in step Ib) is therefore, according to the invention, taken off in the lower part of the distillation column, preferably in the lower fifth of the distillation column and particularly preferably at the bottom of the column or in the range up to a maximum of 5 theoretical plates above this. The content of β-olefins, e.g. 2-butenes, in the stream taken off is usually in the range from 70 to 99.99% by weight and in particular in the range from 85 to 99.9% by weight, based on the sum of $C_i$-olefins having terminal and internal double bonds, e.g. 2-butenes and 1-butene, in the stream taken off. The stream which has been taken off in this way is fed in its entirety or at least in part, e.g. a proportion in the range from 25 to 99% by weight, in particular in the range from 50 to 95% by weight, in each case based on the total weight of the stream taken off, to a first reaction zone.

In the first reaction zone, the stream fed in is reacted in the presence of a double bond isomerization catalyst known per se. The choice of the isomerization catalyst is not subject to any particular restrictions, it merely has to be able to effect the isomerization of linear olefins having an internal double bond, e.g. 2-butenes, to the corresponding linear olefins having a terminal double bond, e.g. 1-butene. For example, basic catalysts or zeolite-based catalysts are used for this purpose, and it is also possible to carry out the isomerization under hydrogenative conditions over catalysts comprising noble metals. Suitable double bond isomerization catalysts are, in particular, alkaline earth metal oxides on aluminum oxide, as are described in EP-A 718036; mixed aluminum oxide/silicon oxide supports which have been doped with oxides of the alkaline earth metals, boron group metals, lanthanides or elements of the iron group, as are described in U.S. Pat. No. 4,814,542; and γ-aluminum oxide laden with alkali metals, as is described in JP 51-108691. Further suitable catalysts are catalysts comprising manganese oxide on aluminum oxide, as described in U.S. Pat. No. 4,289,919; catalysts comprising magnesium, alkali metal and zirconium oxides dispersed on an aluminum oxide support, as described in EP-A 234 498; and aluminum oxide catalysts which further comprise sodium oxide and silicon oxide, as described in U.S. Pat. No. 4,229,610. Suitable zeolite-based catalysts are described in EP-A 129 899 (zeolites of the pentasil type). Molecular sieves exchanged with alkali or alkaline earth metals, as described in U.S. Pat. No. 3,475,511; aluminosilicates as described in U.S. Pat. No. 4,749,819; and zeolites in alkali metal or alkaline earth metal form, as described in U.S. Pat. No. 4,992,613, and those based on crystalline borosilicates as described in U.S. Pat. No. 4,499,326 are also suitable.

The abovementioned double bond isomerization catalysts are usually used in a fixed bed, fluidized bed or moving bed. It has been found to be advantageous for the amount of the stream passed over the catalyst per unit time to be in the range from 0.1 to 40 g per gram of catalyst and per hour. A fixed-bed reactor system through which the stream flows continuously is preferred for the isomerization reaction. Suitable reactors are, for example, tube reactors, shell-and-tube reactors, tray reactors, coil reactors or helical reactors.

The stream taken off from the distillation column in step Ib) can be taken off in gaseous or liquid form. If the stream taken off is liquid, it has to be vaporized before being fed into the first reaction zone. The apparatus used for vaporization is not subject to any particular restriction. Customary types of vaporizer, e.g. natural convection vaporizers or forced circulation vaporizers, are suitable.

Before the gaseous stream of step Ib) goes into the first reaction zone, it generally has to be heated to the desired reaction temperature. It can be heated using customary apparatuses, e.g. plate heat exchangers or shell-and-tube heat exchangers. The reaction in the first reaction zone is endothermic. The isomerization is advantageously carried out at a temperature which ensures a shift in the position of the double bond but, on the other hand, at which secondary reactions such as cracking processes, skeletal isomerizations, dehydrogenations and oligomerizations are largely avoided. The temperature in the first reaction zone is therefore generally in the range from 100 to 700° C., preferably in the range from 150 to 600° C. and particularly preferably in the range from 200 to 500° C. The temperature can be controlled in a customary manner known per se. In addition, the reaction can also be carried out in an adiabatic reaction system. For the purposes of the present invention, this term is used in the industrial and not the physicochemical sense. The pressure is set so that the stream fed to the first reaction zone is gaseous. The pressure is generally in the range from 1 to 40 bar, preferably in the range from 2 to 30 bar and particularly preferably in the range from 3 to 20 bar.

Carbon-comprising compounds can deposit over time on the isomerization catalyst used for the reaction and these can lead to deactivation of the catalyst. Burning-off these deposits makes it possible to increase the activity of the catalyst again. The burning-off procedure can be carried out in a separate apparatus or preferably in the apparatus used for the reaction.

In a specific embodiment, the reactor is designed in duplicate so that, alternately, one apparatus is available for the reaction while the regeneration can be carried out in the other apparatus. To carry out the burning-off procedure, a mixture of inert gases such as nitrogen, helium and/or argon with a proportion of oxygen, in particular a nitrogen/oxygen mixture, is generally passed over the catalyst. The proportion of oxygen in the inert gas, in particular nitrogen, is generally in the range from 1 to 20% by volume. The oxygen content of the mixture can advantageously be altered during the regeneration procedure. A low oxygen content, e.g. in the range from 1 to 10% by volume, is preferably employed at the beginning and this is then increased. This makes control of the amount of heat evolved by the exothermic burning-off process possible. The regeneration is carried out at an elevated temperature which is usually in the range from 300 to 900° C., preferably in the range from 350 to 800° C. and particularly preferably in the range from 400 to 700° C.

The output from the double bond isomerization stage usually has a content of linear $C_i$-olefins having an internal double bond, e.g. 2-butenes, which is from 2 to 50% by weight lower, in particular from 5 to 30% by weight, lower, than the content in the stream fed to the first reaction zone, based on the total weight of the same linear $C_i$-olefins having an internal double bond in the stream fed to the first reaction zone. In step Ic), the output from the double bond isomerization stage is fed back into the distillation column at a point of the distillation column which is above the point at which the stream taken off from the column in step Ib) is taken off. For example, the stream discharged from the isomerization can be recirculated to the distillation column in the region from 1 to 30 theoretical plates above the point at which the stream taken off in step Ib) is taken off.

The output from the double bond isomerization stage can be fed in gaseous or liquid form into the distillation column. If the temperature difference between the stream at the outlet from the first reaction zone and the temperature in the interior of the distillation column at the level of the reintroduction is large, e.g. more than 20° C., it can be useful to cool the output from the isomerization stage. The cooling or condensation is carried out using customary apparatuses known to those skilled in the art.

In the upper part of the distillation column, e.g. in the region of the upper 5 theoretical plates and in particular at the top of the column, a stream enriched in linear $C_i$-olefin having a terminal double bond, e.g. 1-butene, is taken off in step Id). The content of linear $C_i$-olefin having a terminal double bond, e.g. 1-butene, in the stream taken off from the column in step Id) is usually in the range from 60 to 100% by weight and in particular in the range from 80 to 99.99% by weight, in each case based on the sum of $C_i$-olefins having a terminal or internal double bond, e.g. 1-butene and 2-butenes. In particular, the stream taken off in step Id) comprises from 60 to 99.9% by weight of linear olefins having terminal and internal double bonds, from 0.01 to 5% by weight of multiply unsaturated compounds, from 0.01 to 40% by weight of further compounds such as saturated and/or branched hydrocarbons, in particular ones having i carbon atoms. In the case of i=4, the stream taken off in step Id) thus comprises, for example, from 60 to 99.9% by weight of 1-butene and 2-butenes, from 0.01 to 5% by weight of multiply unsaturated compounds, e.g. butadienes, and from 0.01 to 40% by weight of further compounds, e.g. isobutane, n-butane and isobutene.

The abovementioned multiply unsaturated compounds can originate from the olefin-comprising feed used and/or are formed in the reaction in the first reaction zone under particular conditions, in particular when particular double bond isomerization catalysts are chosen. It has therefore been found to be advantageous to subject the stream taken off from the distillation column in step Id) to a selective hydrogenation to reduce the content of multiply unsaturated compounds, e.g. butadienes and alkynes, before it is fed to the second reaction zone. Such a selective hydrogenation can be carried out as mentioned above, as described in EP-81 041 and DE-15 68 542. Otherwise, what has been said above applies analogously to this hydrogenation stage.

To avoid accumulation of high-boiling components, e.g. saturated hydrocarbons having carbon atoms and hydrocarbon compounds having i+1 and more carbon atoms, in the distillation column and/or the first reaction zone, it is generally necessary to bleed off a substream at the bottom of the distillation column or in the region of 5 theoretical plates above this, preferably at the bottom, and discharge it. This stream to be discharged comprises essentially linear $C_i$-olefins having an internal double bond, linear $C_i$-olefins having a terminal double bond, saturated hydrocarbons having i, i+1 and possibly more carbon atoms and possibly multiply ethylenically unsaturated compounds such as dienes or alkynes. If, for example, $C_4$-olefin-comprising feeds are used, this substream comprises essentially 1-butene, 2-butenes, n-butane and hydrocarbons having 5 and more carbon atoms. It is also possible, for the purpose of reducing the amount of high-boiling components, for part of the stream taken off from the column in step Ib) to be discharged from the process. In this case, the stream enriched in linear β-olefins is generally taken off at the bottom of the distillation column. The content of linear $C_i$-olefins having an internal double bond, e.g. 2-butenes, in the substream bled off and discharged is usually in the range from 80 to 99.99% by weight, in particular in the range from 90 to 99.9% by weight, in each case based on the sum of linear $C_i$-olefins having internal and terminal double bonds, e.g. 2-butenes and 1-butene. If a stream for the discharge of high-boiling compounds is bled off separately at the bottom of the distillation column, its content of linear $C_i$-olefins having an internal double bond, e.g. 2-butenes, is usually up to 10% by weight above the content of the same linear $C_i$-olefins having an internal double bond, e.g. 2-butenes, in the stream taken off from the column in step Ib). The size of the stream taken off at the bottom of the column and its content of linear $C_i$-olefins having an internal double bond depends on the total conversion in the conversion of linear β-olefins into linear α-olefins, e.g. 2-butenes into 1-butene, which is preferably in the range from 50 to 99.9% by weight, particularly preferably in the range from 60 to 99.5% by weight and very particularly preferably in the range from 70 to 99% by weight, in each case based on the total weight of linear $C_i$-olefins having an internal double bond in the olefin-comprising feed. The proportion of the stream which is bled off and discharged will advantageously be not more than 5% by weight, in particular not more than 1% by weight and especially not more than 0.1% by weight, and be, for example, in the range from 0.001 to 5% by weight, in particular in the range from 0.005 to 1% by weight, in each case based on the total weight of the stream taken off from the distillation column in step Ib).

Instead of, as just described, discharging part of the stream taken off in step Ib) or a stream taken off separately at the bottom of the distillation column from the process, this substream which has been bled off can also be fed to the abovementioned selective hydrogenation, if such a hydrogenation is provided. This has the additional advantage that the first and second reaction zones remain largely free of components which could adversely affect the catalyst, while at the same time the linear $C_i$-olefins comprised in the stream bled off, in particular ones having a terminal double bond, can be made available for use in the second reaction zone. Such a procedure will be used, in particular, when the stream which has been bled off in the manner described here from the distillation column and fed to the selective hydrogenation is small compared to the stream taken off from the distillation column in step Ib), e.g. accounts for a proportion of not more than 5% by weight, in particular not more than 1% by weight and especially not more than 0.1% by weight and is, for example, in the range from 0.001 to 5% by weight, in particular in the range from 0.005 to 1% by weight, in each case based on the total weight of the stream taken off from the distillation column in step Ib).

In a preferred embodiment, the distillation and isomerization carried out in steps Ia) to Id) are configured so that the heat flows for vaporization and heating are combined with the heat flows for cooling and condensation. Such a heat integration makes it possible to minimize the energy consumption for the reaction unit.

The stream enriched in linear $C_i$-olefin having a terminal double bond which is taken off from the distillation column in step Id) is fed to a second reaction zone. Carbon monoxide and hydrogen are also fed to this second reaction zone. In the second reaction zone, the stream fed in is reacted in the presence of a hydroformylation catalyst. The second reaction zone (hydroformylation stage) can have one or more stages (reaction stages), e.g. two or three stages, and accordingly comprise one or more, identical or different reactors. In the simplest case, the second reaction zone or each reaction stage of the second reaction zone is formed by a single reactor. Both the reactors of each individual stage and the reactors forming the various stages can in each case have identical or different mixing characteristics. The reactors can, if desired, be divided one or more times by means of internals. If two or more reactors form one stage of the reaction system of the second reaction zone, these can be connected with one another in any way, e.g. in parallel or in series. Suitable pressure-rated reaction apparatuses for hydroformylation are known to those skilled in the art. These include the generally customary reactors for gas-liquid reactions, e.g. tube reactors, stirred vessels, gas circulation reactors, bubble columns, etc., which may, if appropriate, be divided by means of internals.

Carbon monoxide and hydrogen are usually used in the form of a mixture known as synthesis gas. The composition of the synthesis gas employed can vary within a wide range. It is possible to set identical or different molar ratios of CO to $H_2$ in the reactor(s) of the second reaction zone or, if appropriate, in the reactors forming the second reaction zone. The molar ratio of carbon monoxide to hydrogen is generally from 1:1000 to 1000:1, preferably from 1:100 to 100:1.

The temperature in the hydroformylation reaction is generally in the range from about 20 to 200° C., preferably from about 50 to 190° C., in particular from about 60 to 180° C. In the case of a multistage configuration of the second reaction zone, it is possible to set, if appropriate, a higher temperature in a subsequent reaction stage than in a preceding reaction stage, e.g. to achieve very complete conversion of olefins which are relatively difficult to hydroformylate. If the second reaction zone or a reaction stage thereof comprises more than one reactor, these can likewise have identical or different temperatures. The reaction in the second reaction zone is preferably carried out at a pressure in the range from about 1 to 700 bar, particularly preferably in the range from 3 to 600 bar and very particularly preferably in the range from 5 to 50 bar. The reaction pressure in the second reaction zone can be varied as a function of the activity of the hydroformylation catalyst used. Thus, the hydroformylation catalysts described in more detail below sometimes allow a reaction in a range of, in particular, relatively low pressures, e.g. in the range from about 1 to 100 bar.

The reactor volume and/or the residence time in the second reaction zone are selected so that generally at least about 10% by weight of the olefins fed in, based on the total olefin content of the stream fed to the hydroformylation stage, is reacted. The conversion based on the amount of olefin in the stream fed to the hydroformylation stage is preferably at least 25% by weight in the second reaction zone.

Suitable hydroformylation catalysts for the second reaction zone (hydroformylation stage) are quite generally the customary transition metal compounds and complexes known to those skilled in the art which can be used both with and without cocatalysts. The transition metal is preferably a metal of transition group VIII of the Periodic Table and in particular Co, Ru, Rh, Pd, Pt, Os or Ir, especially Rh, Co, Ir or Ru.

In the following, the expression "alkyl" comprises straight-chain and branched alkyl groups. Preference is given to straight-chain or branched $C_1$-$C_{20}$-alkyl, more preferably $C_1$-$C_{12}$-alkyl groups, particularly preferably $C_1$-$C_8$-alkyl groups and very particularly preferably $C_1$-$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also comprises substituted alkyl groups which can generally bear 1, 2, 3, 4 or 5 substituents, preferably 1, 2 or 3 substituents and particularly preferably one substituent, selected from among the groups cycloalkyl, aryl, hetaryl, halogen, $NE^1E^2$, $NE^1E^2E^{3+}$, COOH, carboxylate, —$SO_3H$ and sulfonate.

For the purposes of the present invention, the expression "alkylene" refers to straight-chain or branched alkanediol groups having from 1 to 4 carbon atoms.

For the purposes of the present invention, the expression "cycloalkyl" comprises both unsubstituted and substituted cycloalkyl groups, preferably $C_5$-$C_7$-cycloalkyl groups such as cyclopentyl, cyclohexyl or cycloheptyl which, if they are substituted, can generally bear 1, 2, 3, 4 or 5 substituents, preferably 1, 2 or 3 substituents and particularly preferably one substituent, selected from among the groups alkyl, alkoxy and halogen.

For the purposes of the present invention, the expression "heterocycloalkyl" comprises saturated, cycloaliphatic groups which generally have from 4 to 7, preferably 5 or 6, ring atoms and in which 1 or 2 of the ring carbons have been replaced by heteroatoms selected from among the elements oxygen, nitrogen and sulfur and which may optionally be substituted. If they are substituted, these heterocycloaliphatic groups can bear 1, 2 or 3 substituents, preferably 1 or 2 substituents, particularly preferably one substituent, selected from among alkyl, aryl, $COOR^f$, $COO^-M^+$ and $NE^1E^2$, preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl-, tetrahydrothiophenyl, tetrahydrofuranyl, tetrahydropyranyl, dioxanyl.

For the purposes of the present invention, the expression "aryl" comprises unsubstituted and substituted aryl groups and preferably refers to phenyl, tolyl, xylyl, mesityl, naphthyl, fluorenyl, anthracenyl, phenanthrenyl or naphthacenyl, particularly preferably phenyl or naphthyl. If these aryl groups are substituted, they can generally bear 1, 2, 3, 4 or 5 substituents, preferably 1, 2 or 3 substituents and particularly preferably one substituent, selected from among the groups alkyl, alkoxy, carboxyl, carboxylate, trifluoromethyl, —SO$_3$H, sulfonate, NE$^1$E$^2$, alkylene-NE$^1$E$^2$, nitro, cyano and halogen.

For the purposes of the present invention, the expression "hetaryl" refers to unsubstituted or substituted, heterocycloaromatic groups, preferably the groups pyridyl, quinolinyl, acridinyl, pyridazinyl, pyrimidinyl, pyrazinyl, and also the subgroup of "pyrrole group". If these heterocycloaromatic groups are substituted, they can generally bear 1, 2 or 3 substituents selected from among the groups alkyl, alkoxy, carboxyl, carboxylate, —SO$_3$H, sulfonate, NE$^1$E$^2$, alkylene-NE$^1$E$^2$, trifluoromethyl and halogen.

For the purposes of the present invention, the expression "pyrrole group" refers to a series of unsubstituted or substituted, heterocycloaromatic groups which are derived structurally from the pyrrole skeleton and comprise a pyrrole nitrogen in the heterocycle which may be covalently bound to other atoms, for example a pnicogen atom. The expression "pyrrole group" thus comprises the unsubstituted or substituted groups pyrrolyl, imidazolyl, pyrazolyl, indolyl, purinyl, indazolyl, benzotriazolyl, 1,2,3-triazolyl, 1,3,4-triazolyl and carbazolyl. If these are substituted, they can generally bear 1, 2 or 3 substituents, preferably 1 or 2 substituents, particularly preferably one substituent, selected from among the groups alkyl, alkoxy, acyl, carboxyl, carboxylate, —SO$_3$H, sulfonate, NE$^1$E$^2$, alkylene-NE$^1$E$^2$, trifluoromethyl and halogen. A preferred substituted indolyl group is the 3-methylindolyl group.

Accordingly, the expression "bispyrrole group" as used for the purposes of the present invention comprises divalent groups of the formula Py-I-Py, which comprise two pyrrole groups joined by a direct chemical bond or are linked via alkylene, oxa, thio, imino, silyl or alkylimino groups, for example the bisindolediyl group of the formula

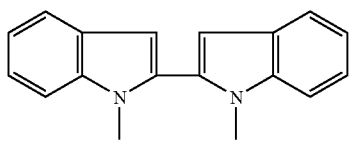 [SMILES: Cn1c(-c2cc3ccccc3n2C)cc2ccccc21]

as an example of a bispyrrole group which comprises two directly bonded pyrrole groups, in this case indolyl, or the bispyrrolediylmethane group of the formula

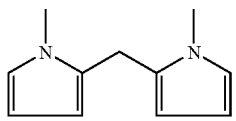

as an example of a bispyrrole group which comprises two pyrrole groups, in this case pyrrolyl, which are linked via a methylene group. Like the pyrrole groups, the bispyrrole groups can also be unsubstituted or substituted and if they are substituted generally bear 1, 2 or 3 substituents, preferably 1 or 2 substituents, in particular one substituent, selected from among alkyl, alkoxy, carboxyl, carboxylate, —SO$_3$H, sulfonate, NE$^1$E$^2$, alkylene-NE$^1$E$^2$, trifluoromethyl and halogen per pyrrole unit. In these indications of the number of possible substituents, the linkage of the pyrrole units by means of a direct chemical bond or the linkage via the abovementioned groups is not considered to be substitution.

For the purposes of the present invention, carboxylate and sulfonate are each preferably a derivative of a carboxylic acid function or a sulfonic acid function, in particular a metal carboxylate or sulfonate, a carboxylic ester or sulfonic ester function or a carboxamide or sulfonamide function. These include, for example, esters with C$_1$-C$_4$-alkanols such as methanol, ethanol, n-propanol, isopropanol, n-butanol, sec-butanol and tert-butanol. They also include primary amides and their N-alkyl and N,N-dialkyl derivatives.

The above explanations of the expressions "alkyl", "cycloalkyl", "aryl", "heterocycloalkyl" and "hetaryl" apply analogously to the expressions "alkoxy", "cycloalkoxy", "aryloxy", "heterocycloalkoxy" and "hetaryloxy".

For the purposes of the present invention, the expression "acyl" refers to alkanoyl or aroyl groups which generally have from 2 to 11, preferably from 2 to 8, carbon atoms, for example the acetyl, propanoyl, butanoyl, pentanoyl, hexanoyl, heptanoyl, 2-ethylhexanoyl, 2-propylheptanoyl, benzoyl or naphthoyl group.

The groups NE$^1$E$^2$, NE$^4$E$^5$, NE$^7$E$^8$, NE$^{10}$E$^{11}$, NE$^{13}$E$^{14}$, NE$^{16}$E$^{17}$, NE$^{19}$E$^{20}$ NE$^2$ E$^{23}$ and NE$^{25}$E$^{26}$ are each preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is preferably fluorine, chlorine, bromine or iodine, preferably fluorine, chlorine or bromine.

M$^+$ is a cation equivalent, i.e. a monovalent cation or the part of a polyvalent cation corresponding to a single positive charge. The cation M$^+$ serves merely as counterion to balance the charge of negatively charged substituent groups, e.g. the COO or sulfonate group, and can in principle be selected freely. Preference is therefore given to using alkali metal ions, in particular Na$^+$, K$^+$, Li$^+$ ions, or onium ions such as ammonium, monoalkylammonium, dialkylammonium, trialkylammonium, tetraalkylammonium, phosphonium, tetraalkylphosphonium or tetraarylphosphonium ions.

An analogous situation applies to the anion equivalent X$^-$ which serves merely as counterion for positively charged substituent groups such as ammonium groups and can be selected freely from among monovalent anions and the parts of polyvalent anions corresponding to a single negative charge. Suitable anions are, for example, halide ions X$^-$, e.g. chloride and bromide. Preferred anions are sulfate and sulfonate, e.g. SO$_4^{2-}$, tosylate, trifluoromethanesulfonate and methylsulfonate.

x is an integer from 1 to 240, preferably an integer from 3 to 120.

Fused ring systems can be aromatic, hydroaromatic and cyclic compounds joined by fusion (condensation). Fused ring systems comprise two, three or more than three rings. Depending on the way in which they are linked, a distinction is made in the case of fused ring systems between ortho-fusion, i.e. each ring shares an edge or two atoms with each adjacent ring, and peri-fusion in which a carbon atom belongs to more than two rings. Among the fused ring systems, preference is given to ortho-fused ring systems.

Preferred complexes comprise at least one phosphorus-comprising compound as ligand. The phosphorus-comprising compounds are preferably selected from among $PF_3$, phospholes, phosphabenzenes, monodentate, bidentate and polydentate phosphine, phosphinite, phosphonite, phosphoramidite, phosphite ligands and mixtures thereof.

The catalysts used according to the invention for the hydroformylation stage can further comprise at least one further ligand which is preferably selected from among halides, amines, carboxylates, acetylacetonate, arylsulfonates and alkylsulfonates, hydride, CO, olefins, dienes, cycloolefins, nitriles, N-comprising heterocycles, aromatics and heteroaromatics, ethers and mixtures thereof.

In general, catalytically active species of the general formula $H_xM_y(CO)_zL_q$, where M is a metal of transition group VIII, L is a phosphorus-comprising compound and q, x, y, z are integers which depend on the valence and type of the metal and on the number of coordination sites occupied by the ligand L, are formed under hydroformylation conditions from the catalysts or catalyst precursors used in each case. Preference is given to z and q each being, independently of one another, at least 1, e.g. 1, 2 or 3. The sum of z and q is preferably from 1 to 5. The complexes can, if desired, additionally bear at least one of the above-described further ligands.

In a preferred embodiment, the hydroformylation catalysts are prepared in situ in the reactor used for the hydroformylation reaction. However, the catalysts used according to the invention can, if desired, also be prepared separately and be isolated by customary methods. To prepare the catalysts according to the invention in situ, it is possible to react, for example, at least one phosphorus-comprising ligand, a compound or a complex of a metal of transition group VIII, if appropriate at least one further additional ligand and, if appropriate, an activator in an inert solvent under the hydroformylation conditions.

Suitable rhodium compounds or complexes are, for example, rhodium (II) and rhodium(III) salts such as rhodium (III) chloride, rhodium(III) nitrate, rhodium(I) sulfate, potassium rhodium sulfate, rhodium(II) or rhodium(III) carboxylate, rhodium(II) and rhodium(III) acetate, rhodium(III) oxide, salts of rhodic(III) acid, trisammonium hexachlororhodate(III), etc. Rhodium complexes such as dicarbonylrhodium acetylacetonate, acetylacetonatobisethylenerhodium(I), etc., are also suitable. Preference is given to using dicarbonylrhodium acetylacetonate or rhodium acetate.

Ruthenium salts or compounds are likewise suitable. Suitable ruthenium salts are, for example, ruthenium(III) chloride, ruthenium(IV) oxide, ruthenium(VI) oxide or ruthenium (VIII) oxide, alkali metal salts of ruthenium oxo acids, e.g. $K_2RuO_4$ or $KRuO_4$, or complexes such as $RuHCl(CO)(PPh_3)_3$. It is also possible to use the metalcarbonyls of ruthenium, e.g. dodecacarbonyltriruthenium or octadecacarbonylhexaruthenium, or mixed forms in which CO is partially replaced by ligands of the formula $PR^3$, e.g. $Ru(CO)_3(PPh_3)_2$, in the process of the invention.

Suitable cobalt compounds are, for example, cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthoate and also the cobalt-caproate complex. Here too, the carbonyl complexes of cobalt, e.g. octacarbonyldicobalt, dodecacarbonyltetracobalt and hexadecacarbonylhexacobalt, can be used.

The abovementioned and further suitable compounds of cobalt, rhodium, ruthenium and iridium are known in principle and are adequately described in the literature or can be prepared by a person skilled in the art using methods analogous to those for the known compounds.

Suitable activators are, for example, Brönsted acids, Lewis acids such as $BF_3$, $AlCl_3$, $ZnCl_2$, $SnCl_2$ and Lewis bases.

As solvent, preference is given to using the aldehydes which are formed in the hydroformylation of the respective olefins and also their high-boiling subsequent reaction products, e.g. the products of the aldol condensation. Further suitable solvents are aromatics such as toluene and xylenes, hydrocarbons or mixtures of hydrocarbons, also for dilution of the abovementioned aldehydes and the subsequent products of the aldehydes. Other solvents are esters of aliphatic carboxylic acids with alkanols, for example ethyl acetate or Texanol™, ethers such as tert-butyl methyl ether and tetrahydrofuran.

Suitable hydroformylation catalysts for the hydroformylation stage are described, for example, in Beller et al., Journal of Molecular Catalysis A, 104 (1995), pp. 17-85, which is hereby fully incorporated by reference.

The catalyst system of the second reaction zone preferably comprises at least one complex of a metal of transition group VIII of the Periodic Table of the Elements with at least one organic phosphorus(III) compound as ligand.

The organic phosphorus(II) compound is preferably selected from among compounds of the general formula $PR^1R^2R^3$, where $R^1$, $R^2$ and $R^3$ are each, independently of one another, alkyl, cycloalkyl, heterocycloalkyl, aryl or hetaryl, with the alkyl radicals being able to bear 1, 2, 3, 4 or 5 substituents selected from among cycloalkyl, heterocycloalkyl, aryl, hetaryl, alkoxy, cycloalkoxy, heterocycloalkoxy, aryloxy, hetaryloxy, COOH, carboxylate, $SO_3H$, sulfonate, $NE^1E^2$, $NE^1E^2E^{3+}+X^-$, halogen, nitro, acyl and cyano, where $E^1$, $E^2$ and $E^3$ are identical or different radicals selected from among hydrogen, alkyl, cycloalkyl and aryl and $X^-$ is an anion equivalent, and the cycloalkyl, heterocycloalkyl, aryl and hetaryl radicals being able to bear 1, 2, 3, 4 or 5 substituents selected from among alkyl and the substituents mentioned above for the alkyl radicals $R^1$, $R^2$ and $R^3$, where $R^1$ and $R^2$ together with the phosphorus atom to which they are bound can also form a 5- to 8-membered heterocycle which may, if appropriate, be additionally fused to one, two or three cycloalkyl, heterocycloalkyl, aryl or hetaryl rings, with the heterocycle and, if present, the fused-on groups each being able to bear, independently of one another, one, two, three or four substituents selected from among alkyl and the substituents mentioned above for the alkyl radicals $R^1$, $R^2$ and $R^3$.

Further suitable organic phosphorus(III) compounds are chelating compounds of the general formula $R^1R^2P-Y^1-PR^1R^2$, where $R^1$ and $R^2$ are as defined above and $Y^1$ is a divalent bridging group. It is possible for the two radicals $R^1$, the two radicals $R^2$ and the two radicals $R^3$ to have identical or different meanings in each case.

The bridging group $Y^1$ is preferably selected from among the groups of the formulae III.a to III.t described below, which are hereby fully incorporated by reference. In a particularly preferred embodiment, $Y^1$ is a group of the formula III.a. In a further particularly preferred embodiment, $Y^1$ is a radical of the formula

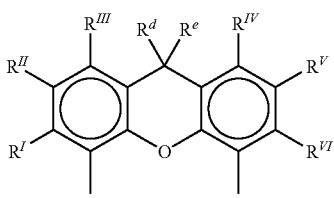

where

R$^I$, R$^{II}$, R$^{III}$, R$^{IV}$, R$^V$ and R$^{VI}$ are each, independently of one another, hydrogen, alkyl, cycloalkyl, heterocycloalkyl, aryl, hetaryl, hydroxy, thiol, polyalkylene oxide, polyalkylenimine, alkoxy, halogen, COOH, carboxylate, SO$_3$H, sulfonate, NE$^7$E$^8$, alkylene-NE$^7$E$^8$, trifluoromethyl, nitro, alkoxycarbonyl, acyl or cyano, where E$^7$ and E$^8$ are identical or different radicals selected from among hydrogen, alkyl, cycloalkyl and aryl, where two adjacent radicals R$^I$ to R$^{VI}$ together with the carbon atoms of the benzene ring to which they are bound can also be a fused ring system having 1, 2 or 3 further rings, and R$^d$ and R$^e$ are each, independently of one another, hydrogen, alkyl, cycloalkyl, heterocycloalkyl, aryl or hetaryl.

Particularly preferred hydroformylation catalysts for use in the second reaction zone are phosphorus-comprising rhodium catalysts as are, for example, formed in situ from a rhodium source and a triarylphosphine, e.g. triphenylphosphine, under the hydroformylation conditions.

The catalysts which are disclosed in WO 00/56451 and are based on at least one phosphinamidite ligand are also suitable for use as catalyst system of the second reaction zone. Also suitable are the catalysts which are described by Veen et al. in Angew. Chem. Int. ed. 1999; 38, 336, and are based on chelating diphosphines having backbones of the xanthene type. Also suitable are the metal complexes having adamantane ligands which are described in WO 01/85661 and the metal complexes based on diphosphine ligands having two bridging phosphaadamantyl radicals or phosphaoxaadamantyl radicals which are described in WO 01/85662. Also suitable are the hydroformylation catalysts described in DE-A-100 23 471. Preferred suitable catalysts are the hydroformylation catalysts which are described in WO 01/58589 and are based on phosphorus-comprising, diary-fused bicyclo[2.2.n] skeletons.

Further suitable organic phosphorus(III) compounds are, in particular, chelating compounds of the general formula I

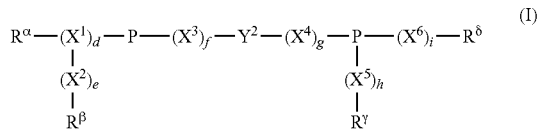
(I)

where

Y$^2$ is a divalent bridging group,

R$^\alpha$, R$^\beta$, R$^\gamma$ and R$^\delta$ are each, independently of one another, alkyl; cycloalkyl, heterocycloalkyl, aryl or hetaryl, with the alkyl radicals being able to bear 1, 2, 3, 4 or 5 substituents selected from among cycloalkyl, heterocycloalkyl, aryl, hetaryl, alkoxy, cycloalkoxy, heterocycloalkoxy, aryloxy, hetaryloxy; hydroxy, thiol, polyalkylene oxide, polyalkylenimine, COOH, carboxylate, SO$_3$H, sulfonate, NE$^{10}$E$^{11}$, NE$^{10}$E$^{11}$E$^{12+}$X$^-$, halogen, nitro, acyl and cyano, where E$^{10}$, E$^{11}$ and E$^{12}$ are identical or different radicals selected from among hydrogen, alkyl, cycloalkyl and aryl and X$^-$ is an anion equivalent, and the cycloalkyl, heterocycloalkyl, aryl and hetaryl radicals R$^\alpha$, R$^\beta$, R$^\gamma$ and R$^\delta$ being able to bear 1, 2, 3, 4 or 5 substituents selected from among alkyl and the substituents mentioned above for the alkyl radicals R$^\alpha$, R$^\beta$, R$^\gamma$ and R$^\delta$, or R$^\alpha$ and R$^\beta$ and/or R$^\gamma$ and R$^\delta$ together with the phosphorus atom and, if present, the groups X$^1$, X$^2$, X$^5$ and X$^6$ to which they are bound, form a 5- to 8-membered heterocycle which may if appropriate be additionally fused with one, two or three cycloalkyl, heterocycloalkyl, aryl or hetaryl groups, with the heterocycle and, if present, the fused-on groups being able to bear, independently of one another, one, two, three or four substituents selected from among alkyl, cycloalkyl, heterocycloalkyl, aryl, hetaryl, hydroxy, thiol, polyalkylene oxide, polyalkylenimine, alkoxy, halogen, COOH, carboxylate, SO$_3$H, sulfonate, NE$^{13}$E$^{14}$, NE$^{13}$E$^{14}$E$^{15+}$X$^-$, nitro, alkoxycarbonyl, acyl and cyano, where E$^{13}$, E$^{14}$ and E$^{15}$ are identical or different radicals selected from among hydrogen, alkyl, cycloalkyl and aryl and X$^-$ is an anion equivalent, X$^1$, X$^2$, X$^3$, X$^4$, X$^5$ and X$^6$ are selected independently from among O, S, SiR$^\epsilon$R$^\xi$ and NR$^\eta$, where R$^\epsilon$, R$^\xi$ and R$^\eta$ are each, independently of one another, hydrogen, alkyl, cycloalkyl, heterocycloalkyl, aryl or hetaryl, and d, e, f, g, h and i are each, independently of one another, 0 or 1.

The bridging group Y$^2$ in the formula I is preferably selected from among the groups of the formulae III.a to III.t described below, which are hereby fully incorporated by reference.

In particular, the chelating phosphorus compounds used as catalyst system of the second reaction zone are selected from among chelating phosphonites, chelating phosphites and chelating phosphoramidites.

Further suitable catalyst systems for use in the second reaction zone are the catalysts described in WO 02/22261, which comprise at least one complex of a metal of transition group VIII with at least one ligand selected from among chelating phosphonites and chelating phosphites having a xanthene skeleton. Also suitable are the chelating pnicogen complexes based on chelating pnicogen compounds as ligands which have a skeleton of the xanthene or triptycene type and are described in WO 02/083695. Also suitable are the catalysts having at least one pyrrole-phosphorus compound as ligand which are described in WO 03/018192. Also suitable are the catalysts described in the German patent application DE 02 43 138.8. The disclosure of the abovementioned documents is fully incorporated by reference.

The catalyst system of the second reaction zone preferably comprises at least one complex of a metal of transition group VIII of the Periodic Table of the Elements with at least one chelating phosphorus compound of the general formula II

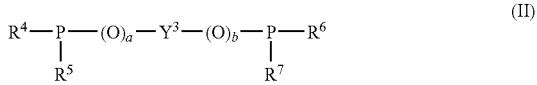
(II)

as ligand, where

R$^4$, R$^5$, R$^6$ and R$^7$ are each, independently of one another, a heteroatom-comprising group which is bound via an oxygen atom or an optionally substituted nitrogen atom to the phosphorus atom or $R^4$ together with $R^5$ and/or $R^6$ together with $R^7$ form a divalent heteroatom-comprising group which is bound via two heteroatoms selected from among oxygen and optionally substituted nitrogen to the phosphorus atom, a and b are each, independently of one another, 0 or 1, and $Y^3$ is a divalent bridging group having from 2 to 20 bridging atoms between the flanking bonds, with at least two bridging atoms being part of an alicyclic or aromatic group.

The individual phosphorus atoms of the chelating phosphorus compounds of the formula II are each joined via two covalent bonds to the substituents $R^4$ and $R^5$ or $R^6$ and $R^7$, where the substituents $R^4$, $R^5$, $R^6$ and $R^7$ are, in a first embodiment, heteroatom-comprising groups which are bound via an oxygen atom or an optionally substituted nitrogen atom to the phosphorus atom, with $R^4$ and $R^5$ or $R^6$ and $R^7$ not being joined to one another. $R^4$, $R^5$, $R^6$ and $R^7$ are then preferably pyrrole groups bound via the pyrrole nitrogen to the phosphorus atom Pn. The meaning of the term pyrrole group here corresponds to the definition given above.

In a further embodiment, $R^4$ together with $R^5$ and/or $R^6$ together with $R^7$ form a divalent heteroatom-comprising group which is bound via two heteroatoms selected from among oxygen and optionally substituted nitrogen to the phosphorus atom. The substituent $R^4$ together with the substituent $R^5$ and/or the substituent $R^6$ together with the substituent $R^7$ can then advantageously form a bispyrrole group bound via the pyrrole nitrogen atoms to the phosphorus atom. Furthermore, the substituent $R^4$ together with the substituent $R^5$ and/or the substituent $R^6$ together with the substituent $R^7$ can form a bridging group bound via two oxygen atoms to the phosphorus atom.

Preference is given to chelating phosphorus compounds in which the radicals $R^4$, $R^5$, $R^6$ and $R^7$ are selected independently from among groups of the formula II.a to II.k:

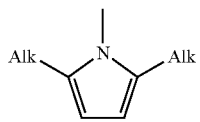   (II.a)

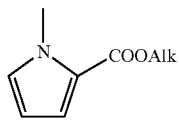   (II.b)

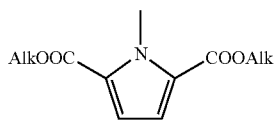   (II.c)

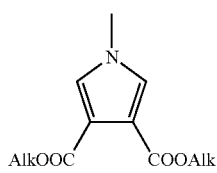   (II.d)

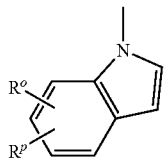   (II.e)

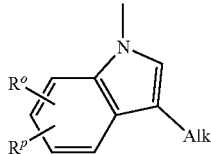   (II.f)

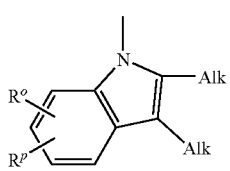   (II.g)

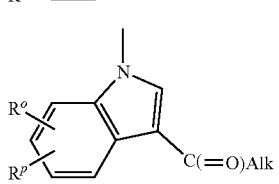   (II.h)

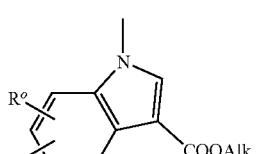   (II.i)

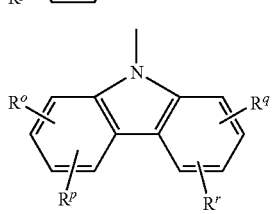   (II.k)

where

Alk is a $C_1$-$C_4$-alkyl group and $R^o$, $R^p$, $R^q$ and $R^r$ are each, independently of one another, hydrogen, $C_1$-$C_4$-alkyl, $C_1$-$C_4$-alkoxy, acyl, halogen, trifluoromethyl, $C_1$-$C_4$-alkoxycarbonyl or carboxyl.

For the purposes of illustration, some advantageous pyrrole groups are listed below:

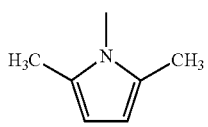   (II.a1)

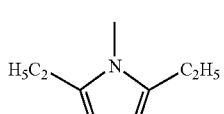   (II.a2)

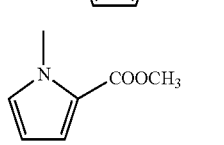   (II.b1)

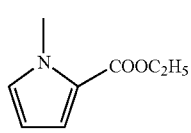   (II.b2)

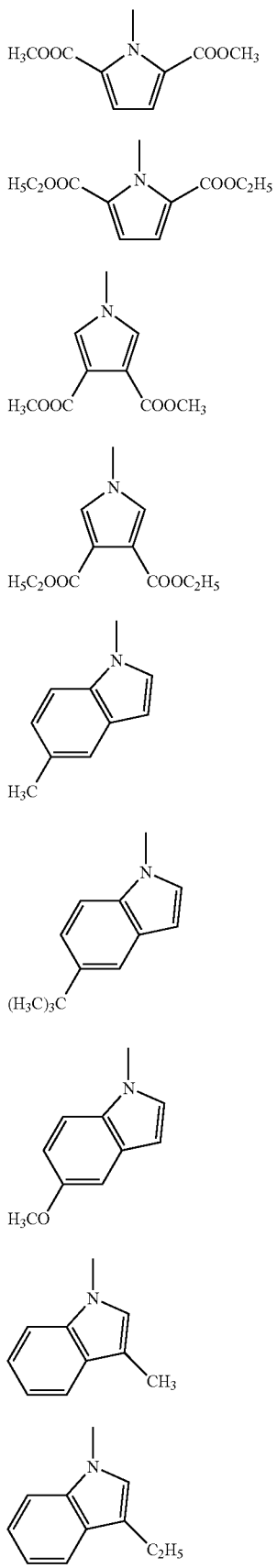
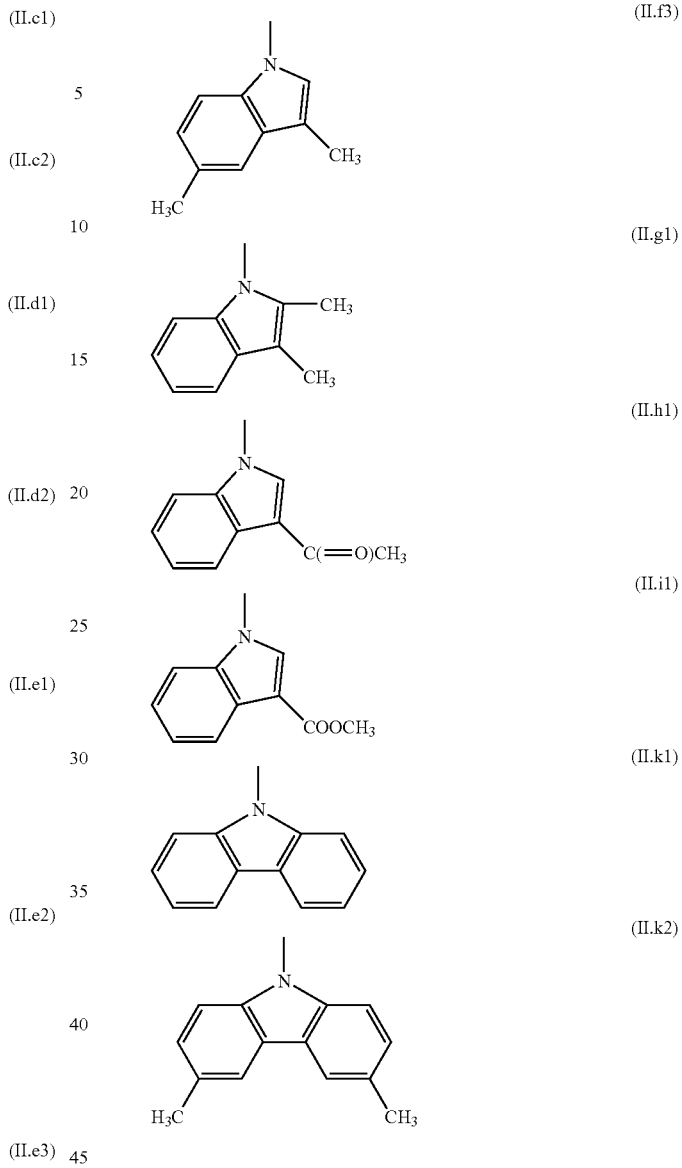

A particularly advantageous pyrrole group is the 3-methylindolyl group (skatolyl group) of the formula II.f1. Hydroformylation catalysts based on ligands which have one or more 3-methylindolyl group(s) bound to the phosphorus atom have a particularly high stability and thus particularly long catalyst operating lives.

In a further advantageous embodiment of the present invention, the substituent $R^4$ together with the substituent $R^5$ or the substituent $R^6$ together with the substituent $R^7$ can form a divalent pyrrole-comprising group of the formula Py-I—W bound via the pyrrole nitrogen to the phosphorus atom,
where
Py is a pyrrole group,
I is a chemical bond or O, S, $SiR^\epsilon R^\xi$, $NR^\eta$ or optionally substituted $C_1$-$C_{10}$-alkylene, preferably $CR^\lambda R^\mu$,
W is cycloalkyloxy or cycloalkylamino, aryloxy or arylamino, hetaryloxy or hetarylamino
and
$R^\epsilon$, $R^\xi$, $R^\eta$, $R^\lambda$ and $R^\mu$ are each, independently of one another, hydrogen, alkyl, cycloalkyl, heterocycloalkyl, aryl or hetaryl, where the terms used here have the meanings explained at the outset.

Preferred divalent groups of the formula

Py-I—W are, for example,

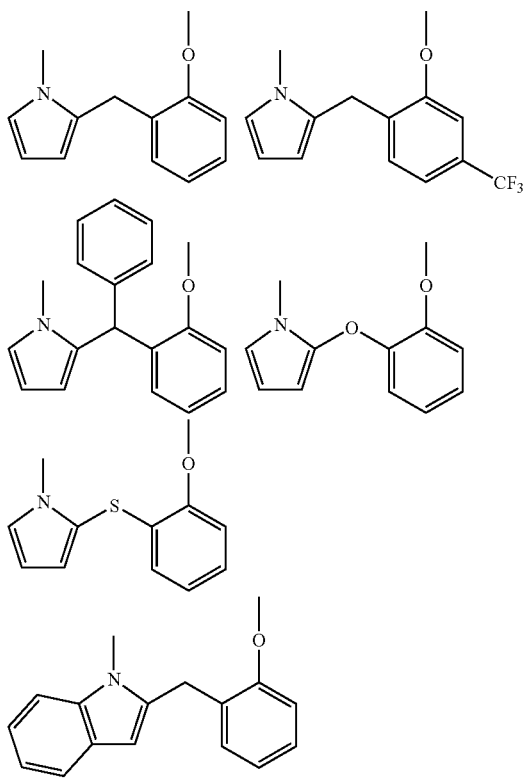

Preference is given to chelating phosphorus compounds in which the substituent $R^4$ together with the substituent $R^5$ or the substituent $R^6$ together with the substituent $R^7$ form a bispyrrole group of the formula

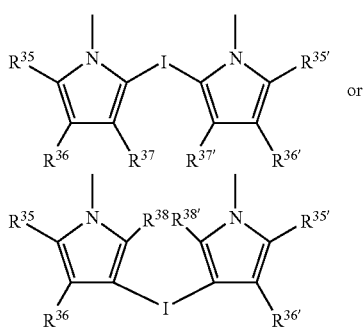

where
I is a chemical bond or O, S, $SiR^\epsilon R^\xi$, $NR^\eta$ or optionally substituted $C_1$-$C_{10}$-alkylene, preferably $CR^\lambda R^\mu$, where $R^\epsilon$, $R^\xi$, $R^\eta$, $R^\lambda$ and $R^\mu$ are each, independently of one another, hydrogen, alkyl, cycloalkyl, heterocycloalkyl, aryl or hetaryl,
$R^{35}$, $R^{35'}$, $R^{36}$, $R^{36'}$, $R^{37}$, $R^{37'}$ $R^{38}$ and $R^{38'}$ are each, independently of one another, hydrogen, alkyl, cycloalkyl, heterocycloalkyl, aryl, hetaryl, W'COOR$^f$, W'COO$^-$M$^+$, W'(SO$_3$) R$^f$, W'(SO$_3$)$^-$M$^+$, W'PO$_3$(R$^f$)(R$^g$), W'(PO$_3$)$^{2-}$(M$^+$)$_2$, W'NE$^{16}$E$^{17}$, W'(NE$^{16}$E$^{17}$E$^{18}$)$^+$X$^-$, W'OR$^f$, W'SR$^f$, (CHR$^9$CH$_2$O)$_x$R$^f$, (CH$_2$NE$^{16}$)$_x$R$^f$, (CH$_2$CH$_2$NE$^{16}$)$_x$R$^f$, halogen, trifluoromethyl, nitro, acyl or cyano,
where
W' is a single bond, a heteroatom, a heteroatom-comprising group or a divalent bridging group having from 1 to 20 bridging atoms,
R$^f$, E$^{16}$, E$^{17}$, E$^{18}$ are identical or different radicals selected from among hydrogen, alkyl, cycloalkyl and aryl,
$R^9$ is hydrogen, methyl or ethyl,
M$^+$ is a cation equivalent,
X$^-$ is an anion equivalent and
x is an integer from 1 to 240,
where two adjacent radicals $R^{35}$ and $R^{36}$ and/or $R^{35'}$ and $R^{36'}$ together with the carbon atoms of the pyrrole ring to which they are bound can also form a fused ring system having 1, 2 or 3 further rings.

I is preferably a chemical bond or a $C_1$-$C_4$-alkylene group, particularly preferably a methylene group.

For the purposes of illustration, some advantageous "bispyrrolyl groups" are listed below:

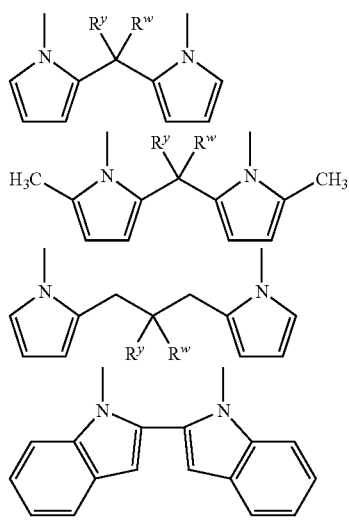

a: R$^y$, R$^w$ = H
b: R$^y$ = H
   R$^w$ = C$_6$H$_5$
c: (R$^y$+R$^w$) = C$_4$H$_8$

Preference is also given to chelating phosphorus compounds of the general formula II in which $R^4$ and $R^5$ and/or $R^6$ and $R^7$ together with the pnicogen atom to which they are bound form a group of the general formula II.A

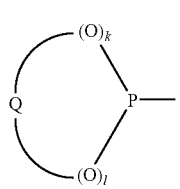

(II.A)

where
k and l are each, independently of one another, 0 or 1,
Q together with the phosphorus atom and the oxygen atoms to which it is bound forms a 5- to 8-membered heterocycle which may, if appropriate, be fused with one, two or three cycloalkyl, heterocycloalkyl, aryl and/or hetaryl groups, with the fused-on groups each being able to bear, independently of one another, one, two, three or four substituents selected from among alkyl, alkoxy, cycloalkyl, aryl, halogen, hydroxy, thiol, polyalkylene oxide, polyalkylenimine, COOH, carboxylate, $SO_3H$, sulfonate, $NE^4E^5$, alkylene-$NE^4E^5$, nitro and cyano, and/or Q may bear one, two or three substituents selected from among alkyl, alkoxy, optionally substituted cycloalkyl and optionally substituted aryl and/or a may be interrupted by 1, 2 or 3 optionally substituted heteroatoms, Depending on whether the group of the general formula II.A is bound to the group $Y^3$ via an oxygen atom (a or b=1) or a covalent bond (a or b=0) and whether k and l are 0 or 1, the chelating phosphorus compounds of the formula II according to the invention thus have at least one phosphine, phosphinite, phosphonite and/or phosphite radical. Preference is given to the groups of the formula II.A being bound to the group $Y^3$ via an oxygen atom and k and l being 1 (phosphite groups).

The radical Q is preferably a $C_2$-$C_6$-alkylene bridge which is fused with one or two aryl groups and/or may bear a substituent selected from among alkyl, optionally substituted cycloalkyl and optionally substituted aryl and/or may be interrupted by an optionally substituted heteroatom.

The fused-on aryls of the radicals Q are preferably benzene or naphthalene. Fused-on benzene rings are preferably unsubstituted or bear 1, 2 or 3, in particular 1 or 2, substituents selected from among alkyl, alkoxy, halogen, $SO_3H$, sulfonate, $NE^4E^5$, alkylene-$NE^4E^5$, trifluoromethyl, nitro, carboxyl, alkoxycarbonyl, acyl and cyano. Fused-on naphthalenes are preferably unsubstituted or have 1, 2 or 3, in particular 1 or 2, of the substituents mentioned above for the fused-on benzene rings in the ring which is not fused on and/or in the fused-on ring. In the substituents of the fused-on aryls, alkyl is preferably $C_1$-$C_4$-alkyl and in particular methyl, isopropyl or tert-butyl. Alkoxy is preferably $C_1$-$C_4$-alkoxy and in particular methoxy. Alkoxycarbonyl is preferably $C_1$-$C_4$-alkoxycarbonyl. Halogen is, in particular, fluorine or chlorine.

When the $C_2$-$C_6$-alkylene bridge of the radical Q is interrupted by 1, 2 or 3 optionally substituted heteroatoms, these are preferably selected from among O, S or $NR^m$, where $R^m$ is alkyl, cycloalkyl or aryl. The $C_2$-$C_6$-alkylene bridge of the radical Q is preferably interrupted by an optionally substituted heteroatom.

When the $C_2$-$C_6$-alkylene bridge of the radical Q is substituted, it preferably has 1, 2 or 3 substituents, in particular 1 substituent, selected from among alkyl, cycloalkyl and aryl, with the aryl substituent being able to bear 1, 2 or 3 of the substituents mentioned for aryl. The alkylene bridge Q preferably bears a substituent selected from among methyl, ethyl, isopropyl, phenyl, p-($C_1$-$C_4$-alkyl)phenyl, preferably p-methylphenyl, p-($C_1$-$C_4$-alkoxy)phenyl, preferably p-methoxyphenyl, p-halophenyl, preferably p-chlorophenyl, and p-trifluoromethylphenyl.

The radical Q is preferably a $C_3$-$C_6$-alkylene bridge which is fused and/or substituted and/or interrupted by optionally substituted heteroatoms as described above. In particular, the radical Q is a $C_3$-$C_6$-alkylene bridge which is fused with 1 or 2 benzene and/or naphthalene groups, with the benzene or naphthalene groups being able to bear 1, 2 or 3, in particular 1 or 2, of the abovementioned substituents.

The radical Q (i.e. $R^4$ and $R^5$ or $R^6$ and $R^7$ together) together with the phosphorus atom and the oxygen atoms to which it is bound preferably forms a 5- to 8-membered heterocycle, with Q ($R^4$ and $R^5$ or $R^6$ and $R^7$ together) being a radical selected from among the radicals of the formulae II.1 to II.5,

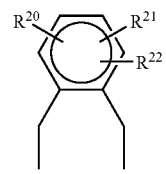

(II.1)

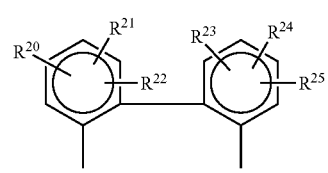

(II.2)

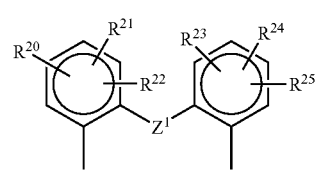

(II.3)

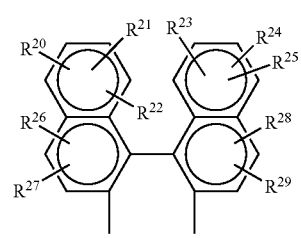

(II.4)

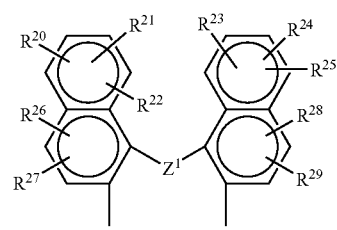

(II.5)

where $Z^1$ is O, S or $NR^m$, where $R^m$ is alkyl, cycloalkyl or aryl, or $Z^1$ is a $C_1$-$C_3$-alkylene bridge which may have a double bond and/or at least one substituent selected from among alkyl, cycloalkyl and aryl substituents, with the alkyl, cycloalkyl or aryl substituents in turn being able to bear one, two or three of the substituents mentioned at the outset for these groups, or $Z^1$ is a $C_2$-$C_3$-alkylene bridge which is interrupted by O, S or $NR^m$, $R^{20}$, $R^{21}$, $R^{22}R^{23}$, $R^{24}$, $R^{25}$, $R^{26}$, $R^{27}$, $R^{28}$ and $R^{29}$ are each, independently of one another, hydrogen, alkyl, cycloalkyl, aryl, alkoxy, halogen, $SO_3H$, sulfonate, $NE^{19}E^{20}$, alkylene-$NE^{19}E^{20}$, trifluoromethyl, nitro, alkoxycarbonyl, carboxyl or cyano, where $E^{19}$ and $E^{20}$ are each, independently of one another, hydrogen, alkyl, cycloalkyl or aryl.

Preference is given to Q being a radical of the formula II.1 in which $R^{20}$, $R^{21}$ and $R^{22}$ are each hydrogen.

Preference is given to Q being a radical of the formula II.2a

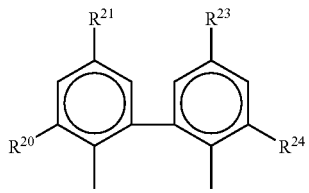
(II.2a)

in which
- $R^{20}$ and $R^{24}$ are each hydrogen, $C_1$-$C_4$-alkyl, $C_1$-$C_4$-alkoxy, $SO_3H$, sulfonate, $NE^9E^{10}$, alkylene-$NE^9E^{10}$, preferably hydrogen, $C_1$-$C_4$-alkyl or $C_1$-$C_4$-alkoxy, in particular methyl, methoxy, isopropyl or tert-butyl,
- $R^{21}$ and $R^{23}$ are each hydrogen, $C_1$-$C_4$-alkyl, preferably methyl, isopropyl or tert-butyl, $C_1$-$C_4$-alkoxy, preferably methoxy, fluorine, chlorine or trifluoromethyl. $R^{21}$ can also be $SO_3H$, sulfonate, $NE^9E^{10}$ or alkylene-$NE^9E^{10}$.

Preference is given to Q being a radical of the formula II.3a

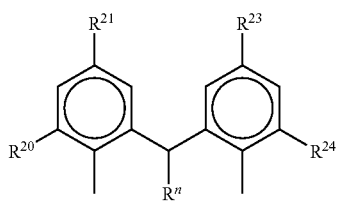
(II.3a)

in which
- $R^{20}$, $R^{21}$, $R^{23}$ and $R^{24}$ have the meanings given above for the formula II.2a,
- $R''$ is hydrogen, $C_1$-$C_4$-alkyl, preferably methyl or ethyl, phenyl, p-($C_1$-$C_4$-alkoxy)phenyl, preferably p-methoxyphenyl, p-fluorophenyl, p-chlorophenyl or p-(trifluoromethyl)phenyl.

Preference is given to Q being a radical of the formula II.4 in which $R^{20}$ to $R^{29}$ are each hydrogen.

Preference is given to Q being a radical of the formula II.4 in which $R^{20}$, $R^2$, $R^{22}$, $R^{23}$, $R^{24}$, $R^{25}$, $R^{27}$ and $R^{29}$ are each hydrogen and the radicals $R^{26}$ and $R^{28}$ are each, independently of one another, alkoxycarbonyl, preferably methoxycarbonyl, ethoxycarbonyl, n-propyloxycarbonyl or isopropyloxycarbonyl. In particular, the radicals $R^{26}$ and $R^{28}$ are located in the ortho position relative to the phosphorus atom or, if present, (k and/or l=1), the oxygen atom.

Preference is given to Q being a radical of the formula II.5 in which $R^{20}$ to $R^{29}$ are each hydrogen and $Z^1$ is $CR''R'''$, where $R''$ and $R'''$ are each, independently of one another, hydrogen, $C_1$-$C_4$-alkyl, preferably methyl or ethyl, phenyl, p-($C_1$-$C_4$-alkoxy)phenyl, preferably p-methoxyphenyl, p-fluorophenyl, p-chlorophenyl or p-(trifluoromethyl)phenyl.

Preference is given to Q being a radical of the formula II.5 in which $R^{20}$, $R^{21}$, $R^{22}$, $R^{23}$, $R^{24}$, $R^{25}$, $R^{27}$ and $R^{29}$ are each hydrogen, $Z^1$ is $CR''R'''$ and the radicals $R^{26}$ and $R^{28}$ are each, independently of one another, alkoxycarbonyl, preferably methoxycarbonyl, ethoxycarbonyl, n-propyloxycarbonyl or isopropyloxycarbonyl. In particular, the radicals $R^{26}$ and $R^{28}$ are located in the ortho position relative to the phosphorus atom or oxygen atom.

In a preferred embodiment, the bridging group $Y^3$ is selected from among groups of the formulae III.a to III.t

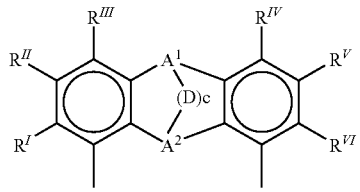
(III.a)

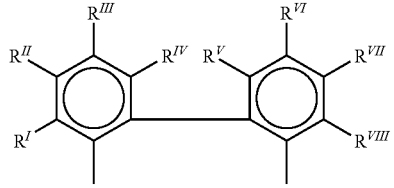
(III.b)

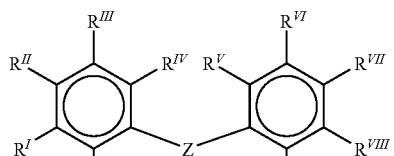
(III.c)

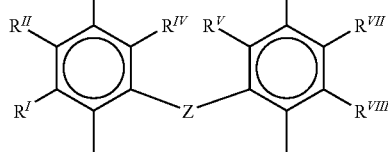
(III.d)

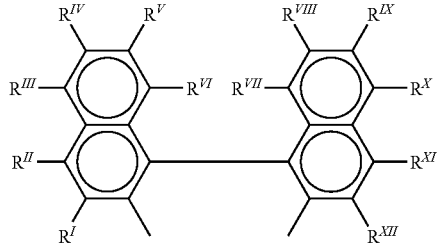
(III.e)

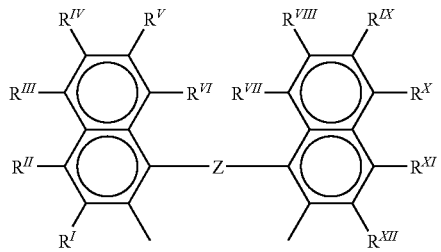
(III.f)

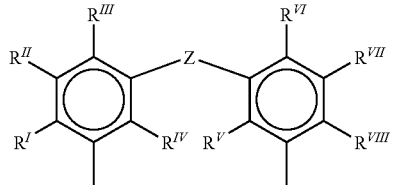
(III.g)

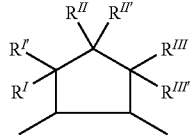
(III.h)

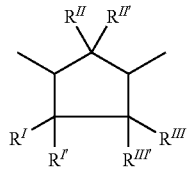

-continued

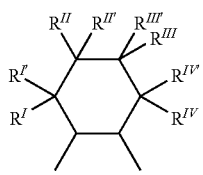
(III.i)

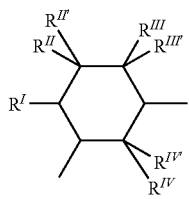
(III.k)

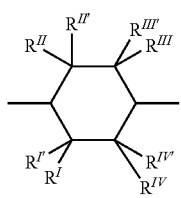
(III.l)

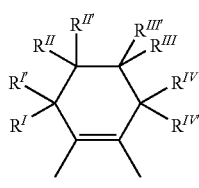
(III.m)

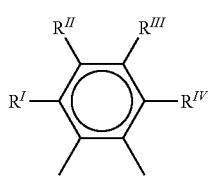
(III.n)

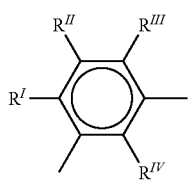
(III.o)

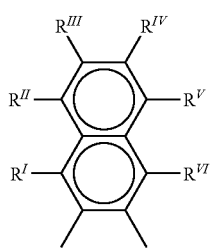
(III.p)

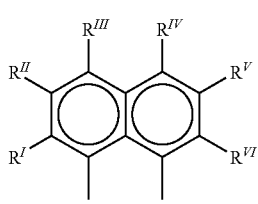

-continued

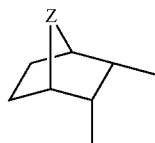
(III.r)

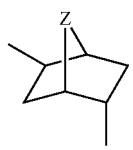
(III.s)

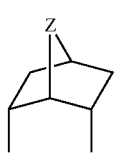
(III.t)

where
$R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$ and $R^{XII}$ are each, independently of one another, hydrogen, alkyl, cycloalkyl, heterocycloalkyl, aryl, hetaryl, hydroxy, thiol, polyalkylene oxide, polyalkyleneimine, alkoxy, halogen, $SO_3H$, sulfonate, $NE^{22}E^{23}$, alkylene-$NE^{22}E^{23}$, trifluoromethyl, nitro, alkoxycarbonyl, carboxyl, acyl or cyano, where $E^{22}$ and $E^{23}$ are identical or different radicals selected from among hydrogen, alkyl, cycloalkyl and aryl, Z is O, S, $NR^{15}$ or $SiR^{15}R^{16}$, where
  $R^{15}$ and $R^{16}$ are each, independently of one another, hydrogen, alkyl, cycloalkyl, heterocycloalkyl, aryl or hetaryl,
  or Z is a $C_1$-$C_4$-alkylene bridge which may have a double bond and/or an alkyl, cycloalkyl, heterocycloalkyl, aryl or hetaryl substituent,
  or Z is a $C_2$-$C_4$-alkylene bridge which is interrupted by O, S or $NR^{15}$ or $SiR^{15}R^{16}$, where, in the groups of the formula III.a, two adjacent radicals $R^I$ to $R^{VI}$, together with the carbon atoms of the benzene ring to which they are bound can also form a fused ring system having 1, 2 or 3 further rings, in the groups of the formulae III.g to III.m, two geminal radicals $R^I$, $R^{I'}$; $R^{II}$, $R^{II'}$; $R^{III}$, $R^{III'}$ and/or $R^{IV}$, $R^{IV'}$ may also represent oxo or a ketal thereof, $A^1$ and $A^2$ are each, independently of one another, O, S, $SiR^aR^b$, $NR^c$ or $CR^dR^e$, where
  $R^a$, $R^b$ and $R^c$ are each, independently of one another, hydrogen, alkyl, cycloalkyl, heterocycloalkyl, aryl or hetaryl,
  $R^d$ and $R^e$ are each, independently of one another, hydrogen, alkyl, cycloalkyl, heterocycloalkyl, aryl or hetaryl or the group $R^d$ together with a further group $R^d$ or the group $R^e$ together with a further group $R^e$ form an intramolecular bridging group D, D is a divalent bridging group of the general formula

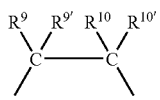

where
  $R^9$, $R^{9'}$, $R^{10}$ and $R^{10'}$ are each, independently of one another, hydrogen, alkyl, cycloalkyl, aryl, halogen, trifluoromethyl, carboxyl, carboxylate or cyano, where $R^{9'}$ together with $R^{10'}$ may also represent the second part of a double bond between the two carbon atoms to which $R^{9'}$ and $R^{10'}$ are bound and/or $R^{9}$ and $R^{10}$ together with the carbon atoms to which they are bound may also form a 4- to 8-membered carbocycle or heterocycle which may if appropriate additionally be fused with one, two or three cycloalkyl, heterocycloalkyl, aryl or hetaryl groups, with the heterocycle and, if present, the fused-on groups each being able, independently of one another, to bear one, two, three or four substituents selected from among alkyl, cycloalkyl, heterocycloalkyl, aryl, hetaryl, $COOR^f$, $COO^-M^+$, $SO_3R^f$, $SO^-_3M^+$, $NE^{25}E^{26}$, alkylene-$NE^{25}E^{26}$, $NE^{25}E^{26}E^{27+}X^-$, alkylene-$NE^{25}E^{26}E^{27+}X^-$, $OR^f$, $SR^f$, $(CHR^9CH_2O)_yR^f$, $(CH_2N(E^{25}))_yR^f$, $(CH_2CH_2N(E^{25}))_yR^f$ halogen, trifluoromethyl, nitro, acyl and cyano, where $R^f$, $E^{25}$, $E^{26}$ and $E^{27}$ are identical or different radicals selected from among hydrogen, alkyl, cycloalkyl and aryl, $R^g$ is hydrogen, methyl or ethyl, $M^+$ is a cation, $X^-$ is an anion and y is an integer from 1 to 120 and c is 0 or 1.

When c=0, the groups $A^1$ and $A^2$ are not joined to one another by a single bond.

The bridging group $Y^3$ is preferably a group of the formula III.a. In the group III.a, the groups $A^1$ and $A^2$ can generally each be, independently of one another, O, S, $SiR^aR^b$, $NR^c$ or $CR^dR^e$, where the substituents $R^a$, $R^b$ and $R^c$ can generally each be, independently of one another, hydrogen, alkyl, cycloalkyl, heterocycloalkyl, aryl or hetaryl while the groups $R^d$ and $R^e$ are each, independently of one another, hydrogen, alkyl, cycloalkyl, heterocycloalkyl, aryl or hetaryl or the group $R^d$ together with a further group $R^d$ or the group $R^e$ together with a further group $R^e$ can form an intramolecular bridging group D.

D is preferably a divalent bridging group selected from among the groups

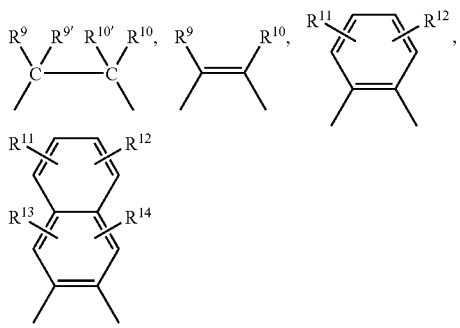

where $R^9$, $R^{9'}$, $R^{10}$ and $R^{10'}$ are each, independently of one another, hydrogen, alkyl, cycloalkyl, aryl, halogen, trifluoromethyl, carboxyl, carboxylate or cyano or are joined to form a $C_3$-$C_4$-alkylene group and $R^{11}$, $R^{12}$, $R^{13}$ and $R^{14}$ can each be, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, aryl and nitro. Preference is given to the groups $R^9$, $R^{9'}$, $R^{10}$ and $R^{10'}$ each being hydrogen, $C_1$-$C_{10}$-alkyl or carboxylate and the groups $R^{11}$, $R^{12}$, $R^{13}$ and $R^{14}$ each being hydrogen, $C_1$-$C_{10}$-alkyl, halogen, in particular fluorine, chlorine or bromine, trifluoromethyl, $C_1$-$C_4$-alkoxy, carboxylate, sulfonate or aryl. $R^9$, $R^{9'}$, $R^{10}$, $R^{10'}$, $R^{11}$, $R^{12}$, $R^{13}$ and $R^{14}$ are particularly preferably each hydrogen. For use in an aqueous reaction medium, preference is given to chelating pnicogen compounds in which 1, 2 or 3, preferably 1 or 2, in particular one, of the groups $R^{11}$, $R^{12}$, $R^{13}$ and/or $R^{14}$ are a $COO^-M^+$, an $SO_3^-M^+$ or a $(NE^1E^2E^3)^+X^-$ group, where $M^+$ and $X^-$ are as defined above.

Particularly preferred bridging groups D are the ethylene group

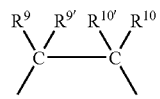

and the 1,2-phenylene group

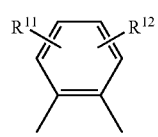

When $R^d$ together with a further group $R^d$ or $R^e$ together with a further group $R^e$ forms an intramolecular bridging group D, i.e. the index c is in this case equal to 1, it follows that both $A^1$ and $A^2$ together form a bridging group, preferably a $CR^dR^e$ group, and the bridging group $Y^3$ of the formula II.a in this case preferably has a triptycene-like or ethanoanthracene-like hydrocarbon skeleton.

Preferred bridging groups $Y^3$ of the formula III.a apart from those having a triptycene-like carbon skeleton are those in which the index c is 0 and the groups $A^1$ and $A^2$ are selected from among the groups O, S and $CR^dR^e$, in particular from among O, S, the methylene group ($R^d$=$R^e$=H), the dimethylmethylene group ($R^d$=$R^e$=$CH_3$), the diethylene group ($R^d$=$R^e$C=$C_2H_5$), the di-n-propylmethylene group ($R^dR^e$=n-propyl) or the di-n-butylmethylene group ($R^d$=$R^e$=n-butyl). In particular, preference is given to bridging groups Y in which $A^1$ is different from $A^2$, with $A^1$ preferably being a $CR^dR^e$ group and $A^2$ preferably being an O or S group, particularly preferably an oxa group O.

Particularly preferred bridging groups $Y^3$ of the formula III.a are thus ones which are made up of a triptycene-like, ethanoanthracene-like or xanthene-like ($A^1$: $CR^dR^e$, $A^2$:O) skeleton.

In the bridging groups $Y^3$ of the formula III.a, the substituents $R^I$, $R^{II}$, $R^{III}$, $R^{IV}$, $R^V$ and $R^{VI}$ are preferably selected from among hydrogen, alkyl, alkoxy, cycloalkyl, heterocycloalkyl, aryl and hetaryl. In a first preferred embodiment, $R^I$, $R^{II}$, $R^{III}$, $R^{IV}$, $R^V$ and $R^{VI}$ are each hydrogen. In a further preferred embodiment, $R^I$ and $R^{VI}$ are each, independently of one another, $C_1$-$C_4$-alkyl or $C_1$-$C_4$-alkoxy. $R^I$ and $R^{VI}$ are preferably selected from among methyl, ethyl, isopropyl, tert-butyl and methoxy. In these compounds, $R^{II}$, $R^{III}$, $R^{IV}$ and $R^V$ are preferably each hydrogen. In a further preferred embodiment, $R^{II}$ and $R^V$ are each, independently of one another, $C_1$-$C_4$-alkyl or $C_1$-$C_4$-alkoxy. $R^{II}$ and $R^V$ are preferably selected from among methyl, ethyl, isopropyl and tert-butyl. In these compounds, $R^I$, $R^{III}$, $R^{IV}$ and $R^{VI}$ are preferably each hydrogen.

When two adjacent radicals selected from among $R^I$, $R^{II}$, $R^{III}$, $R^{IV}$, $R^V$ and $R^{VI}$ in the bridging groups $Y^3$ of the formula III.a form a fused-on ring system, this is preferably a benzene or naphthalene ring. Fused-on benzene rings are preferably unsubstituted or have 1, 2 or 3, in particular 1 or 2, substituents selected from among alkyl, alkoxy, halogen, $SO_3H$, sulfonate, $NE^1E^2$, alkylene-$NE^1E^2$, trifluoromethyl, nitro, $COOR^f$, alkoxycarbonyl, acyl and cyano. Fused-on naphthalene rings are preferably unsubstituted or have a total of 1, 2 or 3, in particular 1 or 2, of the substituents mentioned above for the fused-on benzene rings in the ring which is not fused on and/or in the fused-on ring.

Preference is given to $Y^3$ being a group of the formula III.b in which $R^{IV}$ and $R^V$ are each, independently of one another, $C_1$-$C_4$-alkyl or $C_1$-$C_4$-alkoxy. $R^{IV}$ and $R^V$ are preferably selected from among methyl, ethyl, isopropyl, tert-butyl and methoxy. In these compounds, $R^I$, $R^{II}$, $R^{III}$, $R^{VI}$, $R^{VII}$ and $R^{VIII}$ are preferably each hydrogen.

Preference is also given to $Y^3$ being a group of the formula III.b in which $R^I$ and $R^{VIII}$ are each, independently of one another, $C_1$-$C_4$-alkyl or $C_1$-$C_4$-alkoxy. $R^I$ and $R^{VIII}$ are particularly preferably tert-butyl. In these compounds, $R^{II}$, $R^{III}$, $R^{IV}$, $R^V$, $R^{VI}$, $R^{VII}$ are particularly preferably each hydrogen. Preference is also given to $R^{III}$ and $R^{VI}$ in this compound each being, independently of one another, $C_1$-$C_4$-alkyl or $C_1$-$C_4$-alkoxy. $R^{III}$ and $R^{VI}$ are particularly preferably selected independently from among methyl, ethyl, isopropyl, tert-butyl and methoxy.

Preference is also given to $Y^3$ being a group of the formula III.b in which $R^{II}$ and $R^{VII}$ are each hydrogen. Preference is given to $R^I$, $R^{III}$, $R^{IV}$, $R^V$, $R^{VI}$ and $R^{VIII}$ in these compounds each being, independently of one another, $C_1$-$C_4$-alkyl or $C_1$-$C_4$-alkoxy. $R^I$, $R^{III}$, $R^{IV}$, $R^V$, $R^{VI}$ and $R^{VIII}$ are particularly preferably selected independently from among methyl, ethyl, isopropyl, tert-butyl, and methoxy.

Furthermore, preference is given to $Y^3$ being a group of the formula III.c in which Z is a $C_1$-$C_4$-alkylene group, in particular methylene. Preference is given to $R^{IV}$ and $R^V$ in these compounds each being, independently of one another, $C_1$-$C_4$-alkyl or $C_1$-$C_4$-alkoxy. $R^{IV}$ and $R^V$ are particularly preferably selected independently from among methyl, ethyl, isopropyl, tert-butyl and methoxy. The radicals $R^I$, $R^{II}$, $R^{III}$, $R^{VI}$, $R^{VII}$ and $R^{VIII}$ are preferably each hydrogen.

Preference is also given to $Y^3$ being a group of the formula III.c in which Z is a $C_1$-$C_4$-alkylene bridge which bears at least one alkyl, cycloalkyl or aryl radical. Z is particularly preferably a methylene bridge which bears two $C_1$-$C_4$-alkyl radicals, in particular two methyl radicals. Preference is given to the radicals $R^I$ and $R^{VIII}$ in these compounds each being, independently of one another, $C_1$-$C_4$-alkyl or $C_1$-$C_4$-alkoxy. $R^I$ and $R^{VIII}$ are particularly preferably selected independently from among methyl, ethyl, isopropyl, tert-butyl and methoxy.

Furthermore, preference is given to $Y^3$ being a group of the formula III.d in which $R^I$ and $R^{XIII}$ are each, independently of one another, $C_1$-$C_4$-alkyl or $C_1$-$C_4$-alkoxy. In particular, $R^I$ and $R^{XII}$ are selected independently from among methyl, ethyl, isopropyl, tert-butyl, methoxy and alkoxycarbonyl, preferably methoxycarbonyl. In these compounds, the radicals $R^{II}$ to $R^{XI}$ are particularly preferably each hydrogen.

Preference is also given to $Y^3$ being a group of the formula III.e in which $R^I$ and $R^{XII}$ are each, independently of one another, $C_1$-$C_4$-alkyl or $C_1$-$C_4$-alkoxy. In particular, $R^I$ and $R^{XII}$ are selected independently from among methyl, ethyl, isopropyl, tert-butyl and methoxy. In these compounds, the radicals $R^{II}$ to $R^{XI}$ are particularly preferably each hydrogen.

Furthermore, preference is given to $Y^3$ being a group of the formula III.f in which Z is a $C_1$-$C_4$-alkylene group which bears at least one alkyl, cycloalkyl or aryl substituent. Z is particularly preferably a methylene group which bears two $C_1$-$C_4$-alkyl radicals, especially two methyl radicals. Particular preference is given to the radicals $R^I$ and $R^{VIII}$ in these compounds each being, independently of one another, $C_1$-$C_4$-alkyl or $C_1$-$C_4$-alkoxy. In particular, $R^I$ and $R^{VIII}$ are selected independently from among methyl, ethyl, isopropyl, tert-butyl and methoxy. The radicals $R^{II}$, $R^{III}$, $R^{IV}$, $R^V$, $R^{VI}$ and $R^{VII}$ are preferably each hydrogen.

Preference is also given to $Y^3$ being a group of the formula III.g in which $R^I$, $R^{I'}$, $R^{II}$, $R^{II'}$, $R^{III}$ and $R^{III'}$ are each hydrogen.

Preference is also given to $Y^3$ being a group of the formula III.g in which $R^{II}$ and $R^{II'}$ together form an oxo group or a ketal thereof and the other radicals are each hydrogen.

Preference is also given to $Y^3$ being a group of the formula III.h in which $R^I$, $R^{I'}$, $R^{II}$, $R^{II'}$, $R^{III}$, $R^{III'}$, $R^{IV}$ and $R^{IV'}$ are each hydrogen.

Preference is also given to $Y^3$ being a group of the formula III.h in which $R^{II}$ and $R^{II'}$ together form an oxo group or a ketal thereof and the other radicals are each hydrogen.

Preference is also given to $Y^3$ being a group of the formula III.i in which $R^I$, $R^{I'}$, $R^{II}$, $R^{II'}$, $R^{III}$, $R^{III'}$, $R^{IV}$ and $R^{IV'}$ are each hydrogen.

Preference is also given to $Y^3$ being a group of the formula III.k in which $R^I$, $R^{I'}$, $R^{II}$, $R^{II'}$, $R^{III}$, $R^{III'}$, $R^{IV}$ and $R^{IV'}$ are each hydrogen.

Preference is also given to $Y^3$ being a group of the formula III.l in which $R^I$, $R^{I'}$, $R^{II}$, $R^{II'}$, $R^{III}$, $R^{III'}$, $R^{IV}$ and $R^{IV'}$ are each hydrogen.

Preference is also given to $Y^3$ being a group of the formula III.m in which $R^I$, $R^{I'}$, $R^{II}$, $R^{II'}$, $R^{III}$, $R^{III'}$, $R^{IV}$ and $R^{IV'}$ are each hydrogen.

Preference is also given to $Y^3$ being a group of the formula III.n in which $R^I$, $R^{I'}$, $R^{II}$, $R^{II'}$, $R^{III}$, $R^{III'}$, $R^{IV}$ and $R^{IV'}$ are each hydrogen.

Preference is also given to $Y^3$ being a group of the formula III.n in which one of the radicals $R^I$ to $R^{IV}$ is $C_1$-$C_4$-alkyl or $C_1$-$C_4$-alkoxy. Particular preference is then given to at least one of the radicals $R^I$ to $R^{IV}$ being methyl, ethyl, isopropyl, tert-butyl or methoxy.

Preference is also given to $Y^3$ being a group of the formula III.o in which $R^I$, $R^{II}$, $R^{III}$ and $R^{IV}$ are each hydrogen.

Preference is also given to $Y^3$ being a group of the formula III.o in which one of the radicals $R^I$, $R^{II}$, $R^{III}$ and $R^{IV}$ is $C_1$-$C_4$-alkyl or $C_1$-$C_4$-alkoxy. Particular preference is then given to one of the radicals $R^I$ to $R^{IV}$ being methyl, ethyl, isopropyl, tert-butyl or methoxy.

Preference is also given to $Y^3$ being a group of the formula III.p in which $R^I$ and $R^{VI}$ are each, independently of one another, $C_1$-$C_4$-alkyl or $C_1$-$C_4$-alkoxy. $R^I$ and $R^{VI}$ are particularly preferably selected independently from among methyl, ethyl, isopropyl, tert-butyl and methoxy. $R^{II}$, $R^{III}$, $R^{IV}$ and $R^V$ in these compounds are particularly preferably each hydrogen. Preference is also given to $R^I$, $R^{III}$, $R^{IV}$ and $R^{VI}$ in the compounds III.p each being, independently of one another, $C_1$-$C_4$-alkyl or $C_1$-$C_4$-alkoxy. $R^I$, $R^{III}$, $R^{IV}$ and $R^{VI}$ are then particularly preferably selected independently from among methyl, ethyl, isopropyl, tert-butyl and methoxy.

Preference is also given to $Y^3$ being a group of the formula IIII.q in which $R^I$ and $R^{VI}$ are each, independently of one another, $C_1$-$C_4$-alkyl or $C_1$-$C_4$-alkoxy. $R^I$ and $R^{VI}$ are particularly preferably selected independently from among methyl, ethyl, isopropyl, tert-butyl and methoxy. $R^{II}$, $R^{III}$, $R^{IV}$ and $R^V$ in these compounds are particularly preferably each hydrogen. Preference is also given to $R^{III}$ and $R^{IV}$ in these compounds each being, independently of one another, $C_1$-$C_4$-alkyl or $C_1$-$C_4$-alkoxy. $R^{III}$ and $R^{IV}$ are then particularly preferably selected independently from among methyl, ethyl, isopropyl, tert-butyl and methoxy.

Preference is also given to $Y^3$ being a group of the formula III.r, III.s or III.t in which Z is $CH_2$, $C_2H_2$ or $C_2H_4$.

In the compounds of the formulae III.r, III.s and III.t, it is equally possible for the depicted bonds to the bridged groups to be in endo and exo positions.

The output from the second reaction zone is subjected to work-up, e.g. for the purpose of isolating, concentrating and/or purifying the hydroformylation product, usually a single-stage or multistage separation operation, to give at least a stream comprising the major part of the hydroformylation product and a stream comprising essentially unreacted olefins and possibly saturated hydrocarbons. Saturated hydrocarbons originate, for example, from the olefin-comprising feed used which can comprise these as additional components or to a small extent from the hydrogenation of olefin used. Depending on the discharge and separation processes employed, further streams such as off gases comprising synthesis gas, high-boiling by-products of the hydroformylation and/or streams comprising hydroformylation catalyst may be obtained and these are, if appropriate after work-up, recirculated in their entirety or in part to the second reaction zone or discharged from the process.

A liquid output is preferably taken off from the second reaction zone (liquid discharge process). This liquid output comprises, as significant constituents:
i) the hydroformylation product, i.e. the aldehydes produced from the linear $C_i$-olefins, in particular those having terminal double bonds, which are comprised in the stream fed to the second reaction zone,
ii) the high-boiling by-products of the hydroformylation as result, for example, from the aldol reaction of the aldehydes formed,
iii) the homogeneously dissolved hydroformylation catalyst,
iv) unreacted olefins,
v) low-boiling components such as alkanes and
vi) dissolved synthesis gas.

If an inert solvent such as toluene or xylene is used for the hydroformylation, this too is comprised in the liquid output from the second reaction zone. In general, the by-products having a boiling point higher than that of the hydroformylation product which are formed in the hydroformylation (e.g. by aldol condensation) are used as solvent.

The liquid hydroformylation mixture from the second reaction zone is preferably subjected to a two-stage degassing in order to work it up. Here, the first degassing stage can be a rest and/or depressurization stage. In the simplest embodiment of the first degassing stage as rest zone, the liquid hydroformylation mixture from the second reaction zone is transferred to a vessel which is under the pressure of the reaction zone. Here, it is separated into a first liquid phase and a first gas phase. To separate off the first gas phase with very little liquid, it is possible to provide an appropriate apparatus for removing entrained droplets (demister).

The liquid hydroformylation mixture from the second reaction zone is particularly preferably subjected to a two-stage depressurization in order to work it up. The hydroformylation is preferably carried out at a pressure in the range from 5 to 50 bar. The liquid hydroformylation mixture from the second reaction zone is preferably depressurized to a pressure from 0.1 to 20 bar below the reactor pressure in the first depressurization stage. Here, it is separated into a first liquid phase and a first gas phase. The first liquid phase is preferably depressurized to a pressure lower than the pressure in the first depressurization stage in a second depressurization stage. Here, it is separated into a second liquid phase and a second gas phase.

The partial depressurization in the first depressurization stage can, for example, be carried out in a customary pressure separator. The first gas phase obtained comprises essentially synthesis gas and possibly small amounts of unreacted olefin and/or low-boiling components (saturated hydrocarbons). The first gas phase can be recirculated to a further use in the process of the invention or independently thereof in other processes. Thus, it can, for example, be recirculated to the reactor, usually after compression to the reactor pressure, or, depending on the amount, partly or wholly passed to thermal utilization.

The first liquid phase separated off in the first depressurization stage is then generally discharged as a liquid stream from the depressurization vessel and depressurized to a pressure which is lower than the pressure of the first depressurization stage in a second depressurization stage. In the second depressurization stage, the liquid phase is preferably depressurized to a pressure in the range from 0.01 to 10 bar, preferably from 0.1 to 5 bar. The pressure in the second depressurization stage is generally from 2 to 20 bar lower, in particular from 3 to 15 bar lower, than the pressure in the first depressurization stage.

The first liquid phase obtained from the first rest/depressurization stage is separated in the second depressurization stage (degassing stage) into a second liquid phase and a second gas phase. The second liquid phase comprises the by-products which have boiling points higher than that of the hydroformylation product, the homogeneously dissolved hydroformylation catalyst and part of the hydroformylation product. The second gas phase comprises the unreacted olefins, saturated hydrocarbons and likewise part of the hydroformylation product.

In a preferred embodiment, the second depressurization stage is configured as a combination of a depressurization step (flash step) with a thermal separation step. This thermal separation step can be, for example, a distillation step. Preference is given to feeding the second liquid phase and the second gas phase from the second depressurization step to the distillation in countercurrent and thus bringing them into particularly intimate contact (stripping). The second depressurization step and the thermal separation step can be carried out in separate apparatuses or advantageously in a single apparatus, e.g. in a "flash/stripping column".

When the second depressurization stage has a separate thermal separation, the first liquid phase discharged from the first depressurization stage can firstly be depressurized in a flash vessel. The resultant second gas phase is fed into the bottom or the lower part of a downstream distillation column. The (second) liquid phase from the flash vessel is fed into this distillation column above the point at which the gas phase is fed in. For this purpose, the (second) liquid phase from the flash vessel can, for example, be fed into this distillation column at or just below the top. The second liquid phase can in this case be heated beforehand, for example in a heat exchanger. The second liquid phase is preferably heated to a temperature which is from about 10° C. to 120° C. above the temperature of the liquid phase in the flash vessel (in the second depressurization stage). Suitable columns are the customary distillation columns known to those skilled in the art which are equipped with, for example, random packing elements, ordered packing or internals for intensive gas/liquid exchange.

When the second depressurization stage is configured as a "flash/stripping column", the first liquid phase discharged from the first depressurization stage is fed into a region above the bottom and below the top of the flash/stripping column and thus depressurized. Separation into the second gas phase and the second liquid phase occurs here. The introduction is preferably effected within the lower half, in particular within the lower third, of the flash/stripping column. A liquid stream is taken off at the bottom of the flash/stripping column and fed back into the column at or below the top. The descending liquid phase is thus conveyed in countercurrent to the second gas phase and stripped. The liquid phase can be heated beforehand for this purpose. The liquid phase taken off from the bottom is preferably heated to a temperature which is from about 10° C. to 120° C. above the temperature at the bottom. The columns used preferably have internals for intensive gas/liquid exchange in the upper region, in particular within the upper third.

Both when the second depressurization stage has a separate thermal separation and when a flash/stripping column is used, a third liquid phase comprising the dissolved hydroformylation catalyst and the by-products having boiling points higher than that of the hydroformylation product and a third gas phase comprising the hydroformylation product, the unreacted olefin and saturated hydrocarbons are obtained.

The third liquid phase can, if appropriate after removal of the high boilers in order to avoid accumulation of these, be recirculated to the first reaction zone.

The third gas phase obtained in the second depressurization (stripping) stage is subjected to a separation into a fraction comprising essentially the hydroformylation product and a fraction comprising essentially unreacted olefins and low-boiling components. For this purpose, the third gas phase can be subjected to a fractional condensation. The third gas phase can also be condensed completely and subsequently subjected to a thermal separation. The hydroformylation product is passed to a further use, as described below. The fraction comprising unreacted olefins and low-boiling components can, after condensation, partly be fed as liquid stream to the second depressurization stage and partly discharged from the process or be discharged in its entirety. In a specific embodiment, this fraction is subjected to an additional work-up to separate off at least part of the inert component comprised (saturated hydrocarbons). For this purpose, the fraction can, for example, be subjected to another fractional condensation or complete condensation with subsequent distillation.

In summary, the work-up of the output from step Id) is preferably carried out in an additional step Ie) in which Ie1) the generally liquid output from the second reaction zone, which comprises as significant constituents the hydroformylation product, by-products having boiling points higher than that of the hydroformylation product, the homogeneously dissolved hydroformylation catalyst, unreacted olefins, saturated hydrocarbons and unreacted synthesis gas, is subjected to degassing in which, if appropriate, the pressure and/or the temperature are reduced compared to the reaction zone and which results in a first gas phase comprising essentially the unreacted synthesis gas and a first liquid phase comprising essentially the hydroformylation product, by-products having boiling points higher than that of the hydroformylation product, the homogeneously dissolved hydroformylation catalyst, unreacted olefins and saturated hydrocarbons, Ie2) the first gas phase is passed to a use, Ie3) the first liquid phase is subjected to a depressurization in which the pressure is reduced below that in the first degassing to such an extent that a second gas phase comprising unreacted olefins, saturated hydrocarbons and part of the hydroformylation product and a second liquid phase comprising the by-products having boiling points higher than that of the hydroformylation product, the homogeneously dissolved hydroformylation catalyst and part of the hydroformylation product result, Ie4) the second gas phase is fed into the bottom or the lower part of a column and the second liquid phase is, if appropriate after heating, fed in liquid form into this column at a point above the point at which the gas phase is fed in and is conveyed in countercurrent to the gas phase, Ie5) a third liquid phase comprising essentially the dissolved hydroformylation catalyst and the by-products of the hydroformylation which have boiling points higher than that of the hydroformylation product is taken off at the bottom of the column and a third gas phase comprising the hydroformylation product, unreacted olefins and saturated hydrocarbons is taken off at the top of the column, Ie6) the third liquid phase is, if appropriate after separating off at least part of the by-products having boiling points higher than that of the hydroformylation product, is recirculated to the second reaction zone and Ie7) the third gas phase is subjected to a work-up to give a fraction comprising essentially the hydroformylation product and a fraction comprising essentially unreacted olefins and saturated hydrocarbons.

A schematic overview of a preferred embodiment as described above of the process of the invention with inclusion of the step (I) is shown in FIG. 1. In the description below, reference is made to the figures.

The method of carrying out the process of the invention with inclusion of the process step (II) is described in more detail below.

To carry out the process comprising the process step (II), the olefin-comprising feed is, according to the invention, firstly subjected to the hydroformylation stage before part of the output therefrom, comprising linear $C_i$-olefin having internal double bonds, is fed to the isomerization step. Both the reaction in the hydroformylation stage and that in the isomerization stage can be carried out in the same way as described above for the hydroformylation stage or the isomerization stage in carrying out process step (I), so that in the following description of embodiments comprising the process step (II), reference can accordingly be made thereto.

An aspect common to the various embodiments of the invention comprising the process step (II) is that the content of starting materials, products and by-products in the individual streams should be matched to one another so that, firstly, unnecessary accumulation of by-products and/or unreacted starting materials in the reaction system is avoided but, secondly, the process can be carried out economically. In a preferred embodiment, the process of the invention with inclusion of the process step (II) is therefore carried out as follows:

IIa) the olefin-comprising feed and also carbon monoxide and hydrogen are fed into a first reaction zone and reacted in the presence of a hydroformylation catalyst;

IIb) the stream comprising unreacted linear $C_i$-olefin having an internal double bond is separated off from the output from the first reaction zone and is separated into two fractions of which at least one comprises unreacted linear $C_i$-olefin having an internal double bond;

IIc) the fraction comprising unreacted linear $C_i$-olefin having an internal double bond which is obtained from step IIb) is fed into a second reaction zone and reacted in the presence of a double bond isomerization catalyst; and IId) the output from the second reaction zone is recirculated to step IIa).

With regard to the configuration of the first reaction zone (hydroformylation stage) in step IIa) in process step (II) of the invention, reference is made to what has been said above with regard to the second reaction zone (hydroformylation stage) in process step (I) of the invention. In particular, the single-stage or multistage configurations, reactor types and arrangements, operating parameters such as temperature, pressure, throughputs and residence times and also hydroformylation catalysts and cocatalysts, etc., described there can be used in the same way.

In step IIb), the separation of the stream comprising unreacted linear $C_i$-olefin having an internal double bond from the output from step IIa) can be carried out in a manner analogous to that described above for the work-up of the output from the second reaction zone (hydroformylation stage) in process step (I). In particular, the steps of single-stage or multistage degassing or depressurization and the separation into various streams described there can be carried out in the same way. Accordingly, the procedure will generally be to separate unreacted synthesis gas off from the output from the first reaction zone, e.g. by means of a degassing stage, separating off the hydroformylation catalyst, e.g. by means of a flash/stripping column, and also separating off the $C_{i+1}$-hydroformylation products, e.g. by means of fractional condensation or complete condensation with subsequent distillation. This gives the stream comprising unreacted linear $C_i$-olefin having an internal double bond which is to be separated off in step IIb) and is in turn separated into two fractions, likewise in step IIb).

In a preferred embodiment, the stream comprising unreacted linear $C_i$-olefin having an internal double bond is accordingly separated off from the total output from step IIa) in step IIb) as follows:

IIb1) the generally liquid output from the first reaction zone, which comprises as essential constituents the hydroformylation product, by-products having boiling points higher than that of the hydroformylation product, the homogeneously dissolved hydroformylation catalyst, unreacted olefins, saturated hydrocarbons and unreacted synthesis gas, is subjected to degassing in which, if appropriate, the pressure and/or the temperature are reduced to below those in the reaction zone and which results in a first gas phase comprising essentially the unreacted synthesis gas and a first liquid phase comprising essentially the hydroformylation product, by-products having boiling points higher than that of the hydroformylation product, the homogeneously dissolved hydroformylation catalyst, unreacted olefins and saturated hydrocarbons, IIb2) the first gas phase is passed to a use, IIb3) the first liquid phase is subjected to depressurization in which the pressure is reduced below that in the first degassing to such an extent that a second gas phase comprising unreacted olefins, saturated hydrocarbons and part of the hydroformylation product and a second liquid phase comprising the by-products having boiling points higher than that of the hydroformylation product, the homogeneously dissolved hydroformylation catalyst and part of the hydroformylation product result, IIb4) the second gas phase is fed into the bottom or the lower part of a column and the second liquid phase is, if appropriate after heating, fed in liquid form into this column at a point above that at which the gas phase is fed in and is conveyed in countercurrent to the gas phase, IIb5) a third liquid phase comprising essentially the dissolved hydroformylation catalyst and the by-products of the hydroformylation which have boiling points higher than that of the hydroformylation product is taken off at the bottom of the column and a third gas phase comprising the hydroformylation product, unreacted olefins and saturated hydrocarbons is taken off at the top of the column, IIb6) the third liquid phase is, if appropriate after separating off at least part of the by-products having boiling points higher than that of the hydroformylation product, recirculated to the first reaction zone and IIb7) the third gas phase is subjected to a work-up in which a product phase comprising essentially the hydroformylation product and the stream comprising the unreacted linear $C_i$-olefin having an internal double bond, which further comprises essentially unreacted linear $C_i$-olefins having a terminal double bond and saturated hydrocarbons, are obtained.

The stream comprising unreacted linear $C_i$-olefin having an internal double bond which results from the work-up of the output from step IIa) carried out in step IIb) comprises essentially unreacted olefins and saturated hydrocarbons. This stream is fed to a separation stage for separation into two fractions of which at least one comprises unreacted linear $C_i$-olefin having an internal double bond.

In one embodiment, the separation stage for the separation into two fractions can be configured as a simple flow divider, so that the composition of the two fractions obtained is the same. According to the invention, one of the two fractions obtained in step IIb) is then introduced into step IIc). The other fraction which is not introduced into step IIc) can be discharged from the process and, for example, passed to thermal utilization. The amount of the fraction discharged is usually in the range from 1 to 75% by weight, preferably in the range from 2 to 50% by weight and particularly preferably in the range from 5 to 25% by weight, based on the total weight of the stream comprising unreacted linear $C_i$-olefin having an internal double bond which is separated off in step IIb).

Thus, a particularly preferred embodiment additionally comprises the following step IIb8a) in which IIb8a) the stream comprising unreacted linear Cr-olefin having an internal double bond, which further comprises essentially unreacted linear $C_i$-olefins having a terminal double bond and saturated hydrocarbons, is separated by means of a separation stage into two fractions having the same composition of which one is discharged from the process and the other is introduced into step IIc).

In a further embodiment, the separation stage in step IIb) for separation into two fractions can be configured so that the stream comprising unreacted linear $C_i$-olefin having an internal double bond is separated into a fraction enriched in olefins and a fraction depleted in olefins. Of the fractions obtained in this way, the fraction depleted in olefins can be discharged from the process and, for example, passed to thermal utilization. The other fraction which is enriched in olefins is introduced into step IIc). Such a separation of the stream fed to the separation stage into the fraction enriched in olefin and the fraction depleted in olefin can be effected by subjecting the stream fed to the separation stage to an extractive distillation, a membrane separation process, a separation by selective absorption or a combination of at least two of these measures in the separation stage.

The abovementioned separation of the stream comprising unreacted linear $C_i$-olefin having an internal double bond into a fraction enriched in olefins and a fraction depleted in olefins in step IIb) can, in a specific embodiment, be carried out by extractive distillation. Such extractive distillations are known to those skilled in the art. In general, the extractive distillation is carried out in a polar solvent, in particular a polar organic solvent or a mixture of such polar organic solvents with water. Suitable polar solvents are, for example, the organic solvents monomethylformamide, dimethylformamide, diethylformamide, dimethylacetamide and N-methylpyrrolidinone and also mixtures of one or more thereof with water. In particular cases, when the solvent used has a relatively high boiling point so that decomposition of the components to be extracted can occur during the course of the extractive distillation as a result of the elevated temperatures, e.g. at a temperature of at least 130° C., at least 140° C. or at least 150° C., for example in the case of N-methylpyrrolidinone, water is advantageously added to the organic solvent in order to reduce the boiling point of the solvent. Furthermore, addition of water can in some cases improve the selectivity in the extractive distillation. Apart from N-methylpyrrolidinone/water mixtures, further extractants can advantageously be used. Thus, for example, CN 1 280 976 describes the use of dimethylformamide in combination with a further, low-boiling solvent for the separation of butane/butene mixtures. The ethylenically unsaturated compounds such as olefins, e.g. butenes, generally dissolve significantly better in the abovementioned solvents or solvent mixtures than do the saturated hydrocarbons, e.g. butanes. It is therefore possible to selectively scrub out the major part of the olefins from the stream comprising linear $C_i$-olefins having an internal double bond which is separated off in step IIb) and further comprises essentially linear $C_i$-olefins having a terminal double bond and saturated hydrocarbons. For example, the butenes can largely be scrubbed out selectively from a mixture of butanes and butenes.

The extractive distillation is preferably carried out by selectively scrubbing out the olefins, e.g. butenes, in a first column (scrubber). The saturated hydrocarbons, e.g. butanes, are in this case taken off via the top of the column. The solvent stream laden with olefins can subsequently be degassed in a second column (stripper). The butene fraction is taken off at the top of the stripper. Such processes, e.g. for the separation of butane/butene mixtures, are described, for example, in U.S. Pat. Nos. 5,242,550 and 5,288,370.

The abovementioned separation of the stream comprising unreacted linear $C_i$-olefin having an internal double bond into a fraction enriched in olefins and a fraction depleted in olefins in step IIb) can, in a further specific embodiment, be achieved by means of a membrane separation process. Such membrane separation processes using membranes which separate olefins from saturated hydrocarbons (paraffins) are known to those skilled in the art. Such membranes separate the olefin/paraffin mixture into a fraction which is enriched in olefins and permeates through the membrane, i.e. penetrates the membrane, and a fraction which is depleted in olefins and cannot permeate through the membrane. The first fraction which permeates through the membrane is referred to as permeate, while the latter fraction which is retained by the membrane is referred to as retentate. It is possible to use various types of membranes.

These include, for example, "facilitated transport" membranes whose selectivity is produced by selective n-complexation of the olefin by a suitable metal ion, for example $Ag^+$ or $Cu^+$, incorporated in the membrane. Owing to a concentration gradient, diffusion of the olefin through the membrane takes place (see, for example, Chem. Ing. Tech, 2001, 73, 297), with the olefin being able to move either, if the above-mentioned metal ions are freely mobile within the membrane, in T-complexed form or, if the abovementioned metal ions are not freely mobile within the membrane, by a "hopping" mechanism from one metal ion to an adjacent metal ion. The metal ions mentioned can, for example, be present as counterions to anionic sites, (e.g. sulfonate or carboxylate groups) bound to a polymer, e.g. in a Nafion® membrane laden with $Ag^+$, or as cations of a salt (e.g. nitrate) dissolved in a suitable solvent, e.g. water. In the latter case, the salt solution mentioned is located in the pores of a suitable, preferably hydrophilic membrane and/or in the intermediate space between two membranes (or membrane systems), in which case the retentate is located on the side of the one membrane facing away from the solution mentioned and the permeate being located on the other. In the latter variant, continuous or intermittent replacement of the solution can advantageously be carried out.

A further type of suitable membranes are ones in which the separation is based on preferential adsorption and surface diffusion of the olefin into micropores. These membranes can comprise organic materials or advantageously inorganic materials. Particular suitable materials are, for example, microporous carbon which can be produced by thermal treatment of polymeric materials such as polypropylene or polyimides and ceramic materials having micropores, e.g. zeolites.

A further type of suitable membranes is membranes which comprise one or more polar polymers, in which case separation is effected by the olefins and paraffins to be separated having different solubilities and/or diffusion coefficients in the polymer. Suitable polymers are, for example, polyimides, polyetherimides, polyamides, polyamidoimides, polysulfones, polyether sulfones, polyether ketones, polydialkyl-siloxanes and also mixtures, copolymers or block copolymers thereof. Polymers in which an ionic or covalent crosslinking of the polymer chains has been carried out have been found to be advantageous.

The membranes can be integral asymmetric membranes or composite membranes in which the actual separation layer which effects separation has been applied to one or more mesoporous and/or macroporous support(s). The abovementioned separation layer generally has a thickness of from 0.01 to 100 μm, preferably from 0.1 to 20 μm. The mesoporous and/or macroporous support(s) comprises/comprise one or more organic, in particular polymeric material(s), e.g. carbon, and/or inorganic material(s), in particular ceramic or metal.

The membranes can, for example, be used in the form of flat elements, cushion elements, capillary elements, monochannel tube elements or multichannel tube elements which are known per se to those skilled in the art from other membrane separation processes such as ultrafiltration or reverse osmosis (see, for example, R. Rautenbach, Membranverfahren, Grundiagen der Modul-und Anlagenauslegung, Springer-Verlag, 1997). In the case of membrane elements having a tubular geometry, the separation layer is preferably located on the interior or exterior side of the tube.

The membranes are generally surrounded by one or more housings composed of polymeric, metallic or ceramic material, with the connection between housing and membrane being formed by a sealing polymer (e.g. elastomer) or inorganic material.

The membrane separation process can be carried out in one or more membrane apparatuses. In the case of a plurality of membrane apparatuses, the stream fed in can flow through the individual membrane apparatuses either in succession and/or in parallel. The pressure necessary for carrying out the above-described membrane separation processes can be built up by, for example, compression of a gaseous feed stream by means of compressors known per se to those skilled in the art or by pumping of a liquid feed stream by means of pumps known per se to those skilled in the art. The stream fed in is preferably brought to a pressure in the range from 1 to 200 bar, particularly preferably in the range from 2 to 50 bar and very particularly preferably in the range from 4 to 35 bar. Preferred permeate pressures are in the range from 0.01 to 100 bar, particularly preferably in the range from 0.1 to 50 bar and very particularly preferably in the range from 1 to 20 bar, with the permeate pressure always having to be lower than the pressure of the stream fed in. The desired temperature can be set by means of apparatuses known per se to those skilled in the art before introduction into the membrane apparatus used, with the stream leaving the temperature-setting apparatus and entering the membrane apparatus being able to be liquid, gaseous or be a two-phase mixture of gaseous and liquid phases. If the stream entering the membrane apparatus is liquid, the process is then the special case of pervaporation. The temperature set for the membrane separation process is preferably in the range from −50 to 200° C., particularly preferably in the range from 0 to 120° C. and very particularly preferably in the range from 20 to 80° C.

The membrane separation process can have a single stage, i.e. the permeate from a membrane apparatus or the combined permeates from a plurality of membrane apparatuses through which the feed stream flows successively and/or in parallel forms, without further treatment, the fraction enriched in olefin, e.g. butenes, and the part which does not permeate (retentate) forms, without further treatment, the fraction depleted in olefins. The latter comprises essentially saturated hydrocarbons. It will be self evident to a person skilled in the art that permeate and retentate can also be exchanged in terms of their composition. The membrane process can also have two or more stages, with the permeate from a preceding stage in each case being used as feed for the subsequent stage and the retentate from this (subsequent) stage being mixed into the feed to the first-mentioned (preceding) stage. Such arrangements are known per se and are described, for example, in Sep, Sci. Technol, 1996, 31, 729.

The separation of the olefins from the paraffins can, in a further specific embodiment, also be carried out by selective absorption of the olefins in a solution which comprises metal ions, egg. $Ag^+$, $Cu^+$, and forms π complexes with subsequent desorption of the olefins, as described, for example, in Eldridge, Ind. Eng. Chem. Res. 1993, 32, 2208.

The above-described separation of the stream comprising unreacted linear $C_i$-olefin having an internal double bond preferably results in a fraction enriched in olefins and a fraction depleted in olefins. The latter comprises essentially saturated hydrocarbons. For example, a mixture of butanes and butenes can in this way be separated into a fraction comprising essentially 2-butenes and a fraction comprising essentially n-butane and isobutane.

Thus, a further preferred embodiment additionally comprises the following step IIb8b) in which IIb8b) the stream comprising unreacted linear $C_i$-olefin having an internal double bond, which further comprises essentially unreacted linear $C_i$-olefins having a terminal double bond and saturated hydrocarbons, is separated into a fraction enriched in olefins and a fraction depleted in olefins, of which the fraction enriched in olefins is introduced into step IIc), by subjecting this stream to an extractive distillation, a membrane separation process, a separation by selective absorption or a combination of at least two of these measures.

The additional step IIb8b) is preferably carried out instead of the above step IIb8a). However, it will be self evident to a person skilled in the art that it is also possible to subject the fraction taken off from step IIb8a), which is to be introduced into step IIc), to a separation according to step IIb8b) before it is fed to step IIc). The fraction which is not introduced into step IIc) can be discharged from the process and, for example, be passed to thermal utilization. The olefin-enriched fraction which is introduced into step IIc) usually has a content of linear $C_i$-olefin having an internal double bond of at least 25% by weight, in particular at least 50% by weight and especially at least 70% by weight, based on the total weight of the fraction enriched in olefins. Otherwise, it comprises essentially small proportions, e.g. in the range in each case from 0.1 to 25% by weight and in particular in the range from 0.2 to 15% by weight, of saturated hydrocarbons and/or linear $C_i$-olefin having a terminal double bond, in each case based on the total weight of the fraction enriched in olefins. Further constituents, e.g. multiply unsaturated compounds such as butadienes and alkynes, may be comprised in a total amount of not more than 5% by weight and in particular not more than 1% by weight, in each case based on the total weight of the fraction enriched in olefins.

The fraction comprising unreacted linear $C_i$-olefin having an internal double bond which is obtained from step IIb) and introduced into step IIc) is, in the above-described embodiments, either enriched in olefin (in particular as per steps IIb1) to IIb7) and step IIb8b)) or has a content of olefins which corresponds to the content of olefins in the stream comprising unreacted linear Cr-olefin having an internal double bond which is separated off in step IIb) (in particular as per steps IIb1) to IIb7) and step IIb8a)). The fraction introduced into step IIc) is, according to the invention, fed into a second reaction zone (double bond isomerization). In the second reaction zone, the fraction fed in is reacted in the presence of a double bond isomerization catalyst. As regards the configuration of the second reaction zone (double bond isomerization stage) in step IIc) in process step (II) of the invention, reference is made to what has been said above with regard to the first reaction zone (double bond isomerization stage) in process step (I) of the invention. In particular, the reactor types and systems, operating parameters such as temperature, pressure, throughputs and residence times and also isomerization catalysts, etc., described there can be used in the same way.

The output from the second reaction zone is, in step IId), recirculated to step IIa). For this purpose, it can be advantageous to subject the output from the second reaction zone to a selective hydrogenation as described above in order to reduce the content of multiply unsaturated compounds before it is used in step IIa). If the olefin-comprising feed is also subjected to such a selective hydrogenation before being introduced into step IIa) or before being fed into the first reaction zone, the output from the second reaction zone can advantageously be combined with the olefin-comprising feed before being fed to the selective hydrogenation.

The above-described embodiments of the process of the invention (process steps (I) and (II)) give a stream which comprises essentially the hydroformylation product. The hydroformylation product comprises, in particular, the $C_{i+1}$-hydroformylation products, i.e. preferably linear aldehydes having i+1 carbon atoms. This hydroformylation product can be passed to a further work-up or processing step. In particular, the product streams obtained can immediately be used for further reaction, e.g. for the preparation of propylheptanol. They can, if desired, also be subjected to a further work-up by customary methods known to those skilled in the art, e.g. by distillation, and then be processed further.

The invention further provides a process for preparing 2-propylheptanol, in which i) butene or a butene-comprising $C_4$-hydrocarbon mixture is subjected to a hydroformylation by the above-described process to give an n-valeraldehyde-comprising hydroformylation product;

ii) if appropriate, the hydroformylation product is subjected to a separation to give an n-valeraldehyde-enriched Fraction;

iii) the hydroformylation product obtained in step i) or the n-valeraldehyde-enriched fraction obtained in step ii) is subjected to an aldol condensation;

iv) the products of the aldol condensation are catalytically hydrogenated by means of hydrogen to form alcohols; and v) if appropriate, the hydrogenation products are subjected to a separation to give a fraction enriched in 2-propylheptanol.

Steps i) to v) are explained in more detail below.

i) Hydroformylation

Suitable starting materials for the hydroformylation are, in particular, mixtures of 1-butene with 2-butene and industrially available $C_4$-hydrocarbon streams comprising 1-butene and/or 2-butene. The above-described $C_4$ fractions, which are incorporated by reference here, are preferred.

As hydroformylation catalyst in step i), preference is given to using a rhodium/triphenylphosphine catalyst or a hydroformylation catalyst comprising at least one complex of a metal of transition group VIII with at least one ligand of the general formula II. As regards suitable and preferred ligands of the formula II, what has been said above is incorporated by reference here.

As regards suitable and preferred hydroformylation catalysts, activators, solvents, reaction conditions and reactors for the hydroformylation in step i), the general information given above for hydroformylation is fully incorporated by reference here.

ii) Separation

According to a suitable process variant, the product-enriched streams obtained in step i) are subjected to a further separation to give an n-valeraldehyde-enriched fraction. The separation of the hydroformylation product into an n-valeraldehyde-enriched fraction and a fraction depleted in n-valeraldehyde is carried out by customary methods known to those skilled in the art. Preference is given to distillation using known separation apparatuses, e.g. distillation columns such as tray columns which may, if desired, be equipped with bubble caps, sieve plates, sieve trays, valves, etc., evaporators such as thin film evaporators, falling film evaporators, wiped film evaporators, etc.

iii) Aldol Condensation

Two molecules of $C_5$-aldehyde can be condensed to form $\alpha,\beta$-unsaturated $C_{10}$-aldehydes. The aldol condensation is carried out in a known manner, e.g. in the presence of an aqueous base such as sodium hydroxide or potassium hydroxide. As an alternative, it is also possible to use a heterogeneous basic catalyst such as magnesium oxide and/or aluminum oxide (cf., for example, EP-A 792 862). The condensation of two molecules of n-valeraldehyde results in 2-propyl-2-heptanal. If the hydroformylation product obtained in step i) or after the separation in step ii) comprises further $C_5$-aldehydes such as 2-methylbutanal and possibly 2,2-dimethylpropanal or 3-methylbutanal or traces of other aldehydes, these likewise react in an aldol condensation, resulting in the condensation products of all possible aldehyde combinations, for example 2-propyl-4-methyl-2-hexenal. A proportion of these condensation products, e.g. up to 30% by weight, does not stand in the way of advantageous further processing to give 2-propylheptanol-comprising $C_{10}$-alcohol mixtures suitable as plasticizer alcohols.

iv) Hydrogenation

The products of the aldol condensation can be catalytically hydrogenated by means of hydrogen to give $C_{10}$-alcohols, in particular 2-propylheptanol.

For the hydrogenation of the $C_{10}$-aldehydes to the $C_{10}$-alcohols, the catalysts for the hydroformylation are in principle also suitable, usually at higher temperature; however, preference is generally given to more selective hydrogenation catalysts which are used in a separate hydrogenation stage. Suitable hydrogenation catalysts are generally transition metals such as Cr, Mo, W, Fe, Rh, Co, Ni, Pd, Pt, Ru, etc., or mixtures thereof which can be applied to supports such as activated carbon, aluminum oxide, kieseiguhr, etc., to increase the activity and stability. To increase the catalytic activity, Fe, Co and preferably Ni can be used as metal sponge having a very large surface area, including Raney catalysts. The hydrogenation of the $C_{10}$-aldehydes is carried out under conditions which depend on the activity of the catalyst, preferably at elevated temperatures and superatmospheric pressure. The hydrogenation temperature is preferably from about 80 to 250° C. and the pressure is preferably from about 50 to 350 bar.

The crude hydrogenation product can be worked up by customary methods, e.g. by distillation, to give the $C_{10}$-alcohols.

v) Separation

If desired, the hydrogenation products can be subjected to a further separation to give a fraction enriched in 2-propylheptanol and a fraction depleted in 2-propylheptanol. This separation can be carried out by customary methods known to those skilled in the art, e.g. by distillation. The 2-propylheptanol obtained can be processed further by customary methods known to those skilled in the art to produce plasticizers.

Figure 1:
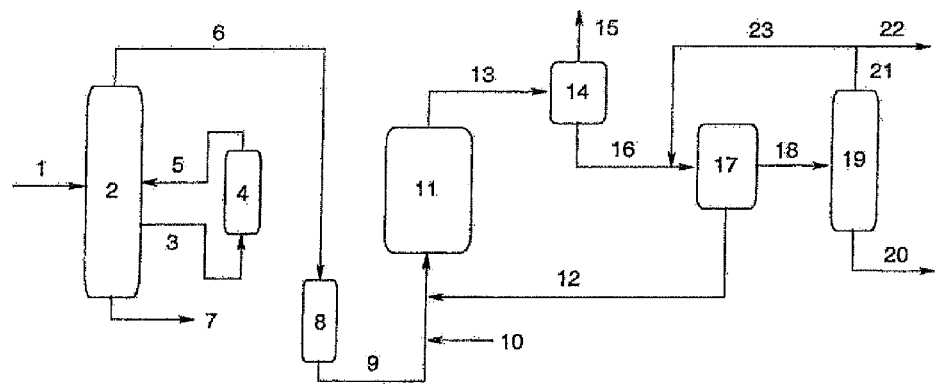
FIG. 1 schemically shows a preferred embodiment of the process of the invention with process step (I). The olefin-comprising feed 1 is fed to a distillation column 2. A stream 3 enriched in linear $C_i$-olefin having an internal double bond is taken off in the lower part of the distillation column 2 and is fed to a first reaction zone 4 (double bond isomerization). In the first reaction zone 4, the stream 3 is reacted in the presence of a double bond isomerization catalyst, resulting in conversion of at least part of the linear $C_i$-olefins having an internal double bond into linear $C_i$-olefins having a terminal double bond. The output 5 from the first reaction zone 4 is fed back into the distillation column 2 at a point on the distillation column 2 which is above the point at which the stream 3 is taken off. A stream 7 enriched in linear $C_i$-olefin having an internal double bond is taken off at the bottom of the distillation column 2 and is discharged from the process. A stream 6 enriched in linear $C_i$-olefin having a terminal double bond is taken off in the upper part of the distillation column 2 and is passed to the selective hydrogenation stage 8. In the hydrogenation stage 8, multiply unsaturated compounds comprised in the stream 6 are selectively hydrogenated to form ethylenically monounsaturated olefins. The output 9 from the hydrogenation stage 8 is conveyed together with carbon monoxide and hydrogen, both fed in via stream 10, and also the output 12 from the separation stage 17, which comprises recovered hydroformylation catalyst, to a second reaction zone 11 (hydroformylation). In the second reaction zone 11, the combined streams 9, 10 and 12 are reacted in the presence of a hydroformylation catalyst. The output 13 comprising the hydroformylation products from the second reaction zone 11 is degassed in the separation stage 14. The offgas from the separation stage 14 is discharged as stream 15. The degassed output 16 from the separation stage 14 is conveyed together with the stream 23 from the separation stage 19, which comprises essentially $C_i$-hydrocarbons, to the separation stage 17.

In the separation stage 17, the hydroformylation catalyst is recovered. The hydroformylation catalyst which has been recovered in this way is recirculated via stream 12 to the second reaction zone 11. The output 18 from the separation stage 17 comprises essentially $C_i$-hydrocarbons, $C_{i+1}$-hydroformylation products and possibly relatively high-boiling compounds. The output 18 is introduced into the separation stage 19 in which the $C_{i+1}$-hydroformylation products and, if appropriate, the relatively high-boiling compounds are separated off and discharged as stream 20. The $C_i$-hydrocarbons are discharged as stream 21 from the separation stage 19 and partly discharged from the process via stream 22 and partly recirculated via stream 23 to the separation stage 17.

Figure 2:
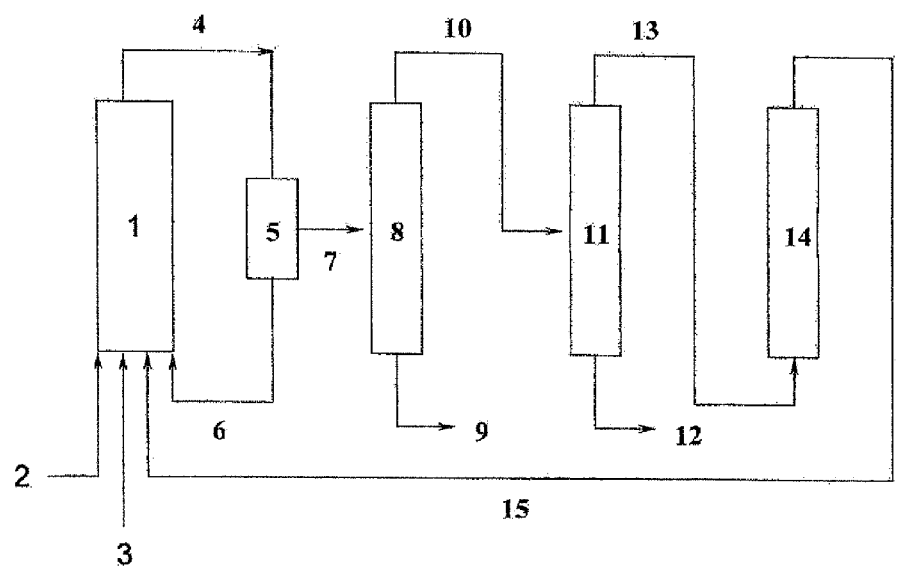

FIG. 2 schematically shows a preferred embodiment of the process of the invention with process step (II). The olefin-comprising feed 2 is fed together with carbon monoxide and hydrogen, both fed in via stream 3, and also the output 6 from the separation stage 5, which comprises recovered hydroformylation catalyst, to a first reaction zone 1 (hydroformylation stage). In addition, the output 15 from the second reaction zone 14 (double bond isomerization), which is enriched in linear $C_i$-olefin having a terminal double bond, is fed into the first reaction zone 1. In the first reaction zone 1, the streams 2, 3, 6 and 15 are reacted in the presence of a hydroformylation catalyst. The output 4 from the first reaction zone comprises essentially $C_{i+1}$-hydroformylation products, possibly compounds having boiling points higher than that of the hydroformylation product, the homogeneously dissolved hydroformylation catalyst, unreacted $C_i$-olefins, saturated $C_i$-hydrocarbons and unreacted synthesis gas. The output 4 is introduced into the separation stage 5, advantageously after a degassing stage to remove the synthesis gas comprised in the output 4 (not shown here). In the separation stage 5, the hydroformylation catalyst is recovered, advantageously by means of, for example, a flash/stripping column. The hydroformylation catalyst which has been recovered in this way is recirculated via stream 6 to the first reaction zone 1; if appropriate, a partial removal of by-products from the stream 6 can additionally be provided (not shown here). The output 7 from the separation stage 5 comprises essentially $C_{i+1}$-hydroformylation products, saturated $C_i$-hydrocarbons, unreacted $C_i$-olefins and possibly compounds which have boiling points higher than that of the hydroformylation product. The output 7 is introduced into the separation stage 8 in which the $C_{i+1}$-hydroformylation products and, if appropriate, the relatively high-boiling compounds are separated off and discharged as stream 9. The output 10 from the separation stage 8, which comprises essentially unreacted olefins and saturated hydrocarbons, is introduced into the separation stage 11 in which the stream 10 is separated into two fractions 12 and 13. The separation stage 11 can here be configured as a simple flow divider, so that the composition of the fractions 12 and 13 is the same and only part of the stream 10 fed in is discharged from the process as stream 12. As an alternative, the separation stage 11 can be configured so that the stream 10 which is fed in is separated into a fraction 13 enriched in olefins, which is fed to the second reaction zone 14 (double bond isomerization) and a fraction 12 depleted in olefins, which is discharged. Such a separation of the stream 10 fed in into the fraction 13 enriched in olefin and the fraction 12 depleted in olefin can be effected by subjecting the stream 10 to an extractive distillation, a membrane separation process, a separation by selective absorption or a combination of at least two of these measures in the separation stage 11. The fraction 13 taken off from the separation stage 11 is fed to the second reaction zone 14. In the second reaction zone 14, the fraction 13 is reacted in the presence of a double bond isomerization catalyst. The output 15 from the second reaction zone 14, which is enriched in linear $C_i$-olefin having a terminal double bond, is recirculated to the first reaction zone 1.

Figure 3:
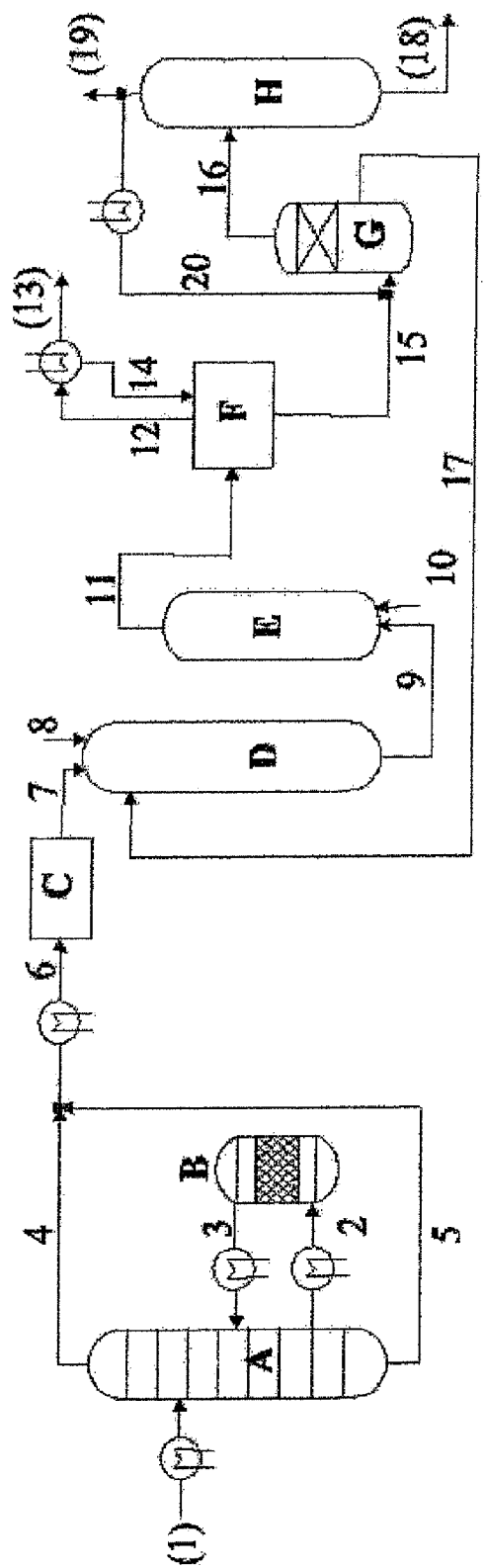

FIG. 3 schematically shows an embodiment of the process of the invention with process step (I), which is explained in detail in example 1. Reference is therefore made to example 1 for the details depicted in FIG. 3.

The invention is illustrated by the following, nonlimiting examples.

EXAMPLES

Unless indicated otherwise, percentages are by weight (% by weight).

Example 1

Variant with Process Step (I)

As regards the way in which the process is carried out, reference is made to FIG. 3. A simulation was carried out using the software CHEMASIM (see http://chemasim.itt.uni-stuttgart.de), under the following assumptions:
  rate constant of the hydroformylation: $k_{HF}$=4.1 h$^{-1}$
  rate constant of the hydrogenation: $k_H$=0.23 h$^{-1}$
  The equilibrium reaction 2-butene $\leftrightarrow$ 1-butene was described via the equilibrium conversion.

A full quantification of the individual streams indicated is shown in table 1 below.

14 t/h of a raffinate II stream 1 (41.5% of 1-butene; 41.5% of 2-butene; further comprising isobutene, isobutane and n-butane) are fed to the distillation column A. In the stripping section of the distillation column A, a stream 2 (comprising 4% of 1-butene; 60% of 2-butene) is taken off and fed to the reactor B. The equilibrium between 1-butene and 2-butene is established in the reactor B at a temperature of 250° C. in the presence of a double bond isomerization catalyst. The output 3 from the reactor B (comprising 10% of 1-butene) is fed back into the distillation column A at a point above the point at which the stream 3 is taken off. A stream 4 (comprising 78% of 1-butene and 4% of 2-butene; conversion of 2-butene=90%, based on the raffinate II stream used) is taken off at the top of the distillation column A. A stream 5 (7 kg/h) is taken off at the bottom of the distillation column A and is combined with the stream 4 to give the stream 6.

Stream 6 is introduced into the hydrogenation stage C. In the hydrogenation stage C, 5% of the 1-butene comprised in the stream 6 is isomerized to 2-butene.

The output 7 from the hydrogenation stage C (comprising 73% of 1-butene) is conveyed together with the synthesis gas stream 8 and the catalyst return stream 17 from the separation stage G to the first hydroformylation reactor D (volume V=140 m$^3$). The output 9 from the first hydroformylation reactor D (partly liquid 9*a*, partly gaseous 9*b*) is fed together with additional synthesis gas 10 into the second hydroformylation reactor E. The reactor E is triply cascaded internally (V=3×per 20 m$^3$).

The output 11 from the second hydroformylation reactor E (partly liquid 11*a*, partly gaseous 11*b*) is separated in the pressure separator F. The offgas stream 12 from the pressure separator F is fed to a condenser in order to condense out $C_4$-hydrocarbons comprised in the offgas stream 12. The remaining offgas stream 13 is passed to a combustion. The condensed-out stream 14 is fed back into the pressure separator F.

The degassed output 15 from the pressure separator F is fed into the lower part of the flasher/stripper G. To achieve a sufficient stripping effect, 8 t/h of $C_4$-hydrocarbons is added to the output 15 via the stream 20 which originates from the hydrocarbon recovery stage H and is heated to a temperature of 90° C. before the output 15 is fed into the flasher/stripper G. In the stripping section of the flasher/stripper G, $C_4$-hydrocarbons and $C_5$-hydroformylation products are separated from the catalyst-comprising bottoms. The stream 12 taken off at the bottom of the flasher/stripper G is recirculated to the first hydroformylation reactor D.

The output 16 comprising $C_4$-hydrocarbons and $C_5$-hydroformylation products is fed to the hydrocarbon recovery stage H where the output 16 is fractionally distilled. The $C_5$-hydroformylation products are taken off at the bottom of the distillation column H and discharged as stream 18 (15 t/h). Part of the $C_4$-hydrocarbons obtained at the top of the distillation column H is discharged via stream 19 (4 t/h). The remaining part of the $C_4$-hydrocarbons obtained at the top of the distillation column H is heated to 90° C. and recirculated via stream 20 (8 t/h) together with stream 15 to the flasher/stripper G.

TABLE 1

| | Stream | | | | | | | |
|---|---|---|---|---|---|---|---|---|
| | 1 | 2 | 3 | 4 | 5 | 6 | 7 | 8 |
| Amount kg/h | 14055 | 85480 | 85479 | 14048 | 7 | 14055 | 14058 | 5431 |
| Isobutane | 0.025000 | 0.000027 | 0.000027 | 0.025013 | 0.000020 | 0.025000 | 0.024995 | — |
| n-Butane | 0.125000 | 0.360219 | 0.360718 | 0.127923 | 0.346289 | 0.128034 | 0.130939 | — |
| 1-Butene | 0.415000 | 0.039719 | 0.100167 | 0.783017 | 0.032191 | 0.782636 | 0.732523 | — |
| c-2-Butene | 0.207500 | 0.243382 | 0.209611 | 0.001981 | 0.259889 | 0.002111 | 0.002111 | — |
| t-2-Butene | 0.207500 | 0.355911 | 0.328269 | 0.039231 | 0.351731 | 0.039389 | 0.089325 | — |
| Isobutene | 0.020000 | 0.000164 | 0.000164 | 0.020010 | 0.000132 | 0.020000 | 0.019996 | — |
| 1,3-Butadiene | — | 0.000413 | 0.000878 | 0.002826 | 0.000349 | 0.002825 | 0.000094 | — |
| H2 | — | — | — | — | — | — | 0.000012 | 0.068444 |
| CO | — | — | — | — | — | — | — | 0.931556 |
| Pentanal | — | — | — | — | — | — | — | — |
| C10 compounds | — | — | — | — | — | — | — | — |
| C15+ compounds | — | — | — | — | — | — | — | — |
| Temperature ° C. | 25.0 | 71.0 | 57.9 | 62.8 | 71.3 | 50 | 90 | 90 |
| Pressure bar | 8.5 | 8.2 | 6.0 | 8.0 | 8.2 | 20 | 19.5 | 20 |
| Enthalpy kW | 218 | 4066 | 10786 | 563 | 0.3 | 443 | 837 | 268 |

| | Stream | | | | | | | |
|---|---|---|---|---|---|---|---|---|
| | 9a | 9b | 10 | 11a | 11b | 12 | 13 | 14 |
| Amount kg/h | 41466 | 1023 | 468 | 41918 | 1039 | 2110 | 838 | 1272 |
| Isobutane | 0.008600 | 0.029272 | — | 0.008477 | 0.030068 | 0.046756 | 0.022386 | 0.062821 |
| n-Butane | 0.057524 | 0.216287 | — | 0.057530 | 0.231944 | 0.366079 | 0.142236 | 0.513637 |
| 1-Butene | 0.020040 | 0.060522 | — | 0.001265 | 0.003986 | 0.006193 | 0.002488 | 0.008636 |
| c-2-Butene | 0.000745 | 0.002319 | — | 0.000733 | 0.002427 | 0.003802 | 0.001228 | 0.005498 |
| t-2-Butene | 0.032278 | 0.081451 | — | 0.031841 | 0.083793 | 0.129741 | 0.041662 | 0.187803 |
| Isobutene | 0.006982 | 0.021804 | — | 0.006883 | 0.022431 | 0.034855 | 0.014966 | 0.047966 |
| 1,3-Butadiene | 0.000033 | 0.000098 | — | 0.000033 | 0.000101 | 0.000156 | 0.000064 | 0.000217 |
| H2 | 0.000088 | 0.029430 | 0.0706368 | 0.000091 | 0.031708 | 0.016906 | 0.042431 | 0.000080 |
| CO | 0.002598 | 0.491586 | 0.9293632 | 0.002630 | 0.519523 | 0.292308 | 0.732042 | 0.002435 |
| Pentanal | 0.451108 | 0.067164 | — | 0.475037 | 0.073950 | 0.103124 | 0.000497 | 0.170776 |
| C10 compounds | 0.369814 | 0.000001 | — | 0.365832 | 0.000001 | 0.000001 | — | 0.000001 |
| C15+ compounds | 0.050186 | 0.000066 | — | 0.049646 | 0.000068 | 0.000078 | — | 0.000130 |
| Temperature ° C. | 90 | 90 | 90 | 90 | 90 | 83.77 | −10 | −10 |
| Pressure bar | 20 | 20 | 20 | 20 | 20 | 8.5 | 8.5 | 8.5 |
| Enthalpy kW | 2093 | 94 | 23 | 2117 | 93 | 232 | 14 | −8 |

| | Stream | | | | | |
|---|---|---|---|---|---|---|
| | 15 | 16 | 17 | 18 | 19 | 20 |
| Amount kg/h | 42119 | 27182 | 22936 | 14946 | 4236 | 8000 |
| Isobutane | 0.008732 | 0.035310 | 0.001534 | 0.000034 | 0.078399 | 0.078399 |
| n-Butane | 0.060147 | 0.242817 | 0.010811 | 0.000035 | 0.539372 | 0.539372 |
| 1-Butene | 0.001308 | 0.005234 | 0.000251 | 0.000009 | 0.011616 | 0.011616 |
| c-2-Butene | 0.000765 | 0.003042 | 0.000156 | 0.000001 | 0.006757 | 0.006757 |
| t-2-Butene | 0.032927 | 0.129212 | 0.007239 | 0.000500 | 0.286431 | 0.286431 |
| Isobutene | 0.007105 | 0.028496 | 0.001339 | 0.000041 | 0.063254 | 0.063254 |
| 1,3-Butadiene | 0.000034 | 0.000135 | 0.000007 | — | 0.000299 | 0.000299 |
| H2 | 0.000028 | 0.000127 | — | — | 0.000282 | 0.000282 |
| CO | 0.000866 | 0.003867 | 0.000003 | — | 0.008590 | 0.008590 |
| Pentanal | 0.474586 | 0.549402 | 0.222134 | 0.995089 | 0.005000 | 0.005000 |
| C10 compounds | 0.364087 | 0.000047 | 0.668529 | 0.000086 | — | — |
| C15+ compounds | 0.049410 | 0.002310 | 0.087997 | 0.004201 | — | — |
| Temperature ° C. | 83.77 | 102.32 | 89.5 | 146.9 | 35.22 | 90 |
| Pressure bar | 8.5 | 1.2 | 1.2 | 3.2 | 3.2 | 1.2 |
| Enthalpy kW | 1973 | 4375 | 1015 | 1426 | 476 | 1112 | c-2-Butene = cis 2-butene
t-2-Butene = trans-2-butene
C10 compounds = compounds having 10 carbon atoms
C15+ compounds = compounds having 15 or more carbon atoms

Example 2

Variant with Process Step (II)

A crude C$_4$ stream from a naphtha cracker is fed in its entirety to a selective hydrogenation stage in which multiply unsaturated compounds such as 1,3-butadiene, alkynes and allenes are hydrogenated to alkenes. Most of the isobutene comprised in the output from the hydrogenation stage is subsequently separated off.

The raffinate stream obtained in this way is combined with the stream E obtained from the double bond isomerization stage to form the stream A. The stream A is reacted with synthesis gas in the presence of an Rh/triphenylphosphane catalyst in the hydroformylation stage. Here, 90% of the 1-butene is reacted in the hydroformylation stage. 3.3% of the 1-butene reacted is isomerized to 2-butenes and 3.3% is hydrogenated to butane. 165 000 t/a of C$_5$-aldehydes are separated off from the output from the hydroformylation stage and are discharged via stream B.

16.5% of the C$_4$ stream C remaining after the C$_5$-aldehydes have been separated off is discharged from the process. The part of the stream C which is not discharged is introduced into the double bond isomerization stage. The double bond isomerization is carried out at a temperature of 350° C. over a potassium oxide/aluminum oxide catalyst.

The output from the double bond isomerization stage is recirculated via stream E, which is combined with the raffinate stream to form stream A, to the hydroformylation stage.

Table 2 below shows the individual streams indicated in metric tons per annum [t/a].

TABLE 2*

| | Raffinate stream | Stream A | Stream C | Stream E |
|---|---|---|---|---|
| Isobutene | 3 000 | 18 000 | 18 000 | 15 000 |
| 1-Butene | 90 000 | 128 000 | 13 000 | 38 000 |
| 2-Butenes | 60 000 | 218 000 | 222 000 | 158 000 |
| Butanes | 7 000 | 63 000 | 67 000 | 56 000 |

*Streams in metric tons per annum [t/a]

The invention claimed is:

1. A process for preparing 2-propylheptanol which comprises
   i) subjecting a mixture of 1-butene and 2-butene or a C$_4$-hydrocarbon mixture comprising 1-butene and 2-butene to a hydroformylation comprising subjecting an olefin-comprising feed to a hydroformylation, wherein the content of linear C$_i$-olefin having a terminal double bond in the stream fed to the hydroformylation stage is increased by means of a double bond isomerization by
   Ia) feeding the olefin-comprising feed to a distillation column;
   Ib) taking off the stream enriched in linear C$_i$-olefin having an internal double bond in the lower part of the distillation column, at least part of the stream taken off is fed to a first reaction zone and reacting in the presence of a double bond isomerization catalyst;
   Ic) recirculating the output from the first reaction zone to the distillation column at a point above that at which the stream taken off in step Ib) is taken off; and
   Id) taking off a stream enriched in linear C$_i$-olefin having a terminal double bond in the upper part of the distillation column, the stream taken off is fed together with carbon monoxide and hydrogen to a second reaction zone and reacting in the presence of a hydroformylation catalyst or
   IIa) feeding the olefin-comprising feed and also carbon monoxide and hydrogen a into a first reaction zone and reacting in the presence of a hydroformylation catalyst;
   IIb) separating off the stream comprising unreacted linear C$_i$-olefin having an internal double bond from the output from the first reaction zone and separating into two fractions of which at least one comprises unreacted linear C$_i$-olefin having an internal double bond;
   IIc) feeding the fraction comprising unreacted linear C$_i$-olefin having an internal double bond which is obtained from step IIb) into a second reaction zone and reacting in the presence of a double bond isomerization catalyst; and
   IId) recirculating the output from the second reaction zone to step IIa) and
   wherein the isomerization catalyst and the hydroformylation catalyst are different catalysts,
   to give an n-valeraldehyde-comprising hydroformylation product;
   ii) subjecting the hydroformylation product to a separation to give an n-valeraldehyde-enriched fraction;
   iii) subjecting the hydroformylation product obtained in step i) or the n-valeraldehyde-enriched fraction obtained in step ii) to an aldol condensation;
   iv) catalytically hydrogenating the products of the aldol condensation by means of hydrogen to form alcohols; and
   v) optionally, subjecting the hydrogenation products to a separation to give a fraction enriched in 2-propylheptanol.

* * * * *